United States Patent
Asama et al.

(10) Patent No.: US 8,423,386 B2
(45) Date of Patent: Apr. 16, 2013

(54) BLOOD SUGAR MEASURED LEVEL MANAGEMENT SYSTEM AND BLOOD SUGAR LEVEL MEASUREMENT APPARATUS

(75) Inventors: Koichiro Asama, Ashigarakami-gun (JP); Yoshihisa Sugawara, Ashigarakami-gun (JP); Hiroyuki Myoujou, Ashigarakami-gun (JP); Hiroko Horiguchi, Ashigarakami-gun (JP); Ryouichi Yoshinari, Hadano (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 361 days.

(21) Appl. No.: 12/745,811

(22) PCT Filed: Dec. 16, 2008

(86) PCT No.: PCT/JP2008/072816
§ 371 (c)(1),
(2), (4) Date: Jun. 2, 2010

(87) PCT Pub. No.: WO2009/081790
PCT Pub. Date: Jul. 2, 2009

(65) Prior Publication Data
US 2010/0268052 A1    Oct. 21, 2010

(30) Foreign Application Priority Data

Dec. 20, 2007 (JP) ................. 2007-329056

(51) Int. Cl.
*G06F 19/00* (2006.01)
(52) U.S. Cl.
USPC ............................................................ 705/3
(58) Field of Classification Search ............. 705/3, 187; 375/316; 455/566; 713/300
See application file for complete search history.

(56) References Cited

U.S. PATENT DOCUMENTS 6,119,238 A * 9/2000 Jennings et al. ............... 713/300
6,792,292 B1 * 9/2004 Chatani ......................... 455/566
(Continued)

FOREIGN PATENT DOCUMENTS

JP    10-019888 A    1/1998
JP    10-318928 A    12/1998
(Continued)

OTHER PUBLICATIONS

International Search Report (PCT/ISA/210) issued on Jan. 27, 2009 by Japanese Patent Office acting as the International Searching Authority for International Application No. PCT/JP2008/072816.
(Continued)

*Primary Examiner* — John Pauls
(74) *Attorney, Agent, or Firm* — Buchanan Ingersoll & Rooney PC

(57) ABSTRACT

The present invention is made to prevent accident of mistaking blood glucose meter among a plurality of blood glucose meters used in a hospital ward.

The blood glucose meter is provided with a nickname area in a nonvolatile storage thereof, and the nickname area can be written from outside. Further, when the blood glucose meter is powered on, a nickname is displayed on a display thereof. A measurement data managing device is provided with a blood glucose meter individual setting table in which the serial number and the nickname of the blood glucose meter are is register in association with each other. When the measurement data managing device is connected with the blood glucose meter and communication is started, the serial number of the blood glucose meter is automatically read out, and the nickname obtained from the blood glucose meter individual setting table is displayed on the display.

8 Claims, 24 Drawing Sheets

U.S. PATENT DOCUMENTS

2003/0158707 A1\* 8/2003 Doi .............................. 702/187
2005/0220221 A1\* 10/2005 Grignani et al. .............. 375/316

FOREIGN PATENT DOCUMENTS

| JP | 2005-080765 A | 3/2005 |
| JP | 2007-159682 A | 6/2007 |
| WO | 99/27849 A1 | 6/1999 |
| WO | WO 01/93143 A1 | 12/2001 |
| WO | WO 2006/098702 A1 | 9/2006 |

OTHER PUBLICATIONS

Extended European Search Report issued Feb. 21, 2013 by the European Patent Office in European Application No. 08865278.9 (10 pgs).

\* cited by examiner

FIG. 12

1106 BLOOD GLUCOSE METER
INDIVIDUAL SETTING TABLE

| SERIAL NUMBER | |
|---|---|
| NICKNAME | |
| VARIOUS SET VALUES | SET VALUE A |
| | SET VALUE B |
| | SET VALUE C |
| | ⋮ |

FIG. 20

| | METER SERIAL NO. | NICKNAME |
|---|---|---|
| 1 | 00000001 | NISHI 5F |
| 2 | 00000002 | NISHI 4F |
| 3 | 00000003 | HIGASHI 5F |
| 4 | 00000004 | HIGASHI 4F |
| 5 | 00000005 | KITA 8F |
| 6 | 00000009 | NISHI 5F |

NICKNAME MANAGEMET

DELETE

RETURN

2003

2002

BLOOD SUGAR MEASURED LEVEL MANAGEMENT SYSTEM AND BLOOD SUGAR LEVEL MEASUREMENT APPARATUS

TECHNICAL FIELD

The present invention relates to a technique preferably applied to a blood glucose level managing system (a blood sugar measured level management system) and a blood glucose measuring device (a blood sugar level measurement apparatus).

More particularly, the present invention relates to a blood glucose measuring device capable of measuring blood glucose for a plurality of patients and administering insulin to the patients in hospital in a safe and reliable manner, and a blood glucose level managing system including the blood glucose measuring device.

BACKGROUND ART

As is well known, diabetes results from inappropriate secretion of insulin by the pancreas. Thus, it is necessary to measure the blood glucose level for a diabetic patient before meals, and administer insulin to the patient according to the measured level.

Conventionally, there has been a small sized blood glucose measuring device developed, manufactured and marketed by the applicant of the present invention, the blood glucose level being designed for measuring blood glucose of a patient at home by the patient himself/herself or by a family member of the patient. Patent applications relating to the blood glucose measuring device are disclosed in Patent Documents 1 and 2.

[Patent Document 1] Japanese Unexamined Patent Application Publication No. H10-19888

[Patent Document 2] Japanese Unexamined Patent Application Publication No. H10-318928

DISCLOSURE OF THE INVENTION

Problems to be Solved by the Invention

It has been reported that the blood glucose measuring device designed for home use is actually used as it is in clinical practice in hospitals where many patients are hospitalized.

However, the blood glucose measuring device designed for home use only has a function of measuring blood glucose, and there are no safety measures for preventing accidents such as patient misidentification, duplicated administration of insulin and the like.

Further, in the blood glucose measuring device designed for home use, functions for improving efficiency of medical practice, such as collectively performing blood glucose measurement process and collectively performing insulin administration process on many patients, are not taken into consideration.

Nowadays, a new blood glucose measuring device having improved functions in terms of safety, efficiency and the like is desired in order to meet the needs of medical practice.

When used in hospitals, it is supposed that there are a plurality of blood glucose measuring devices being used. If a plurality of blood glucose measuring devices of the same shape are placed adjacent to each other, it will be difficult to know which is which. For this reason, there is a high possibility that the blood glucose measuring devices may be mistaken.

To prevent such accident from happening, it is proposed that the medical professionals such as nurses and the like working in medical facilities should put a seal or the like on each other the blood glucose measuring devices, and name each of the blood glucose measuring devices.

However, there is an extremely high possibility that the seal may become a breeding ground for bacteria.

Since the blood glucose measuring devices comes in contact with blood, they are prone to be contaminated with bacteria. Thus, the blood glucose measuring devices need to undergo maintenance such as disinfecting with alcohol on a constant basis. For this reason, the case of the blood glucose measuring device is subjected to a drip-proof treatment so as to become suitable for disinfecting with alcohol.

In the case where the seal is stuck on the case subjected to the drip-proof treatment, even though the disinfecting with alcohol is performed, there is a high possibility that bacteria may enter the gap between the case and the adhesive applied on the sticking surface of the seal, and therefore disinfection effect can not be obtained. This can be a cause of hospital infections. Also, since alcohol has the effect of dissolving adhesive, there is possibility that the seal may be peeled off due to performing disinfecting with alcohol. For the aforesaid reasons, the method of sticking a seal or the like on the case is far from being a good idea.

The present invention is made in view of the above-mentioned problems, and an object of the present invention is to provide a new blood glucose level managing system and a new blood glucose measuring device, which are sanitary and capable of preventing accident of mistaking the blood glucose measuring device.

To solve the aforesaid problems, a blood glucose level managing system according to an aspect of the present invention includes: a blood glucose measuring device; and a measurement data managing device, wherein the blood glucose measuring device includes: a nonvolatile storage having a serial number area in a predetermined area therein for storing a serial number; a read control section adapted to read out the serial number from the serial number area upon receiving a predetermined instruction; and a first communication section connected to the read control section and adapted to perform data communication with an external device, and wherein the measurement data managing device includes: a second communication section adapted to perform communication with the first communication section; a blood glucose measuring device individual setting table having a serial number field for storing the serial number and a nickname field for storing a nickname; a blood glucose measuring device detecting section connected to the second communication section and adapted to detect the establishment of the communication between the first communication section and the second communication section; a blood glucose measuring device operating section adapted to acquire the nickname by transmitting, in response to the fact that the blood glucose measuring device detecting section has detected the establishment of the communication between the first communication section and the second communication section, an instruction to the read control section to instruct it to read out the serial number from the serial number area, and searching the blood glucose measuring device individual setting table using the serial number received from the read control section; and a first display adapted to display the nickname acquired by the blood glucose measuring device operating section.

Further, it is preferred that the nonvolatile storage of the blood glucose measuring device has a nickname area which can only be written from outside.

Further, when the blood glucose measuring device is powered on, the nickname is displayed on a display thereof.

Furthermore, the measurement data managing device is provided with the blood glucose measuring device individual setting table in which the serial number and the nickname of the blood glucose measuring device are is register in association with each other. When the measurement data managing device is connected with the blood glucose measuring device and communication is started, the serial number of the blood glucose measuring device is automatically read out, and the nickname obtained from the blood glucose measuring device individual setting table is displayed on the display.

Further, a blood glucose measuring device according to another aspect of the present invention includes: a power switch; a power control section adapted to receive the operation of the power switch and control power on/off; a nonvolatile storage having a serial number area in a predetermined area therein for storing a serial number and a nickname area in a predetermined area therein for storing a nickname; a display adapted to display a predetermined character string and the like; a read control section adapted to read out the nickname from the nickname area in response to a power-on state notification issued from the power control section and control the display to display the nickname, and at the same time to read out the serial number from the serial number area in response to a power-on state notification issued from the power control section upon receiving a predetermined instruction; and a communication section connected to the read control section and adapted to transmit the serial number to an external device.

Further, it is preferred that the blood glucose measuring device according to the present invention further includes a write control section connected to the communication section and adapted to record a nickname character string in the nickname area only when receiving the nickname character string from the external device through the communication section.

Further, it is preferred that the blood glucose measuring device according to the present invention further includes a power terminal and a voltage detecting section adapted to detect the voltage applied to the power terminal, wherein the power control section performs power-off control in response to the fact that the voltage detecting section no longer detects the voltage after detecting the voltage.

Further, it is preferred that the blood glucose measuring device according to the present invention further includes an operating section connected to the read control section, wherein the read control section reads out the nickname from the nickname area in response to a predetermined operation performed from the operating section, and controls the display to display the nickname.

Although the blood glucose measuring device can be uniquely identified by the serial number, there is no reason for the user to remember the serial number. To solve this problem, in the measurement data managing device, the serial number and the nickname are associated with each other and registered, together with the set values, in the blood glucose measuring device individual setting table. Further, when the communication between the blood glucose measuring device and the measurement data managing device is established, the serial number will be read out from the blood glucose measuring device, the blood glucose measuring device individual setting table will be searched with the serial number to read out the nickname, and the nickname will be displayed on the display. Owing to such a configuration, the user can easily identify the blood glucose measuring device handled by the measurement data managing device.

Further, when deleting the record of the blood glucose measuring device once having been registered in the measurement data managing device, the blood glucose measuring device can be easily identified owing to the existence of the nickname.

The blood glucose measuring device of the blood glucose level managing system according to the present invention has the nickname area provided in the nonvolatile storage thereof, and the nickname can be recorded in the nickname area only from the measurement data managing device. Further, the nickname is displayed in the LCD making use of the time while the self-check is performed when turning on the power. Owing to this configuration, the blood glucose meter can be identified when power is being turned on.

Further, by imposing a restriction on nickname writing to only allow the nickname to be written from the measurement data managing device, the accident of mistaking the blood glucose measuring device can be prevented.

Advantages of the Invention

According to the present invention, it is possible to provide a blood glucose level managing system and a blood glucose measuring device, which are sanitary and capable of preventing accident of mistaking the blood glucose measuring device.

BRIEF DESCRIPTION OF DRAWINGS

FIG. 12 is a view showing each field of a blood glucose meter individual setting table.

FIG. 20 is a view showing a nickname management window.

FIG. 24 is a flowchart showing processing of the blood glucose meter when power is turned on.

BEST MODES FOR CARRYING OUT THE INVENTION

An embodiment of the present invention will be described below with reference to FIGS. 1 to 25.

[Blood Glucose Measuring System 101]

Figure 1:
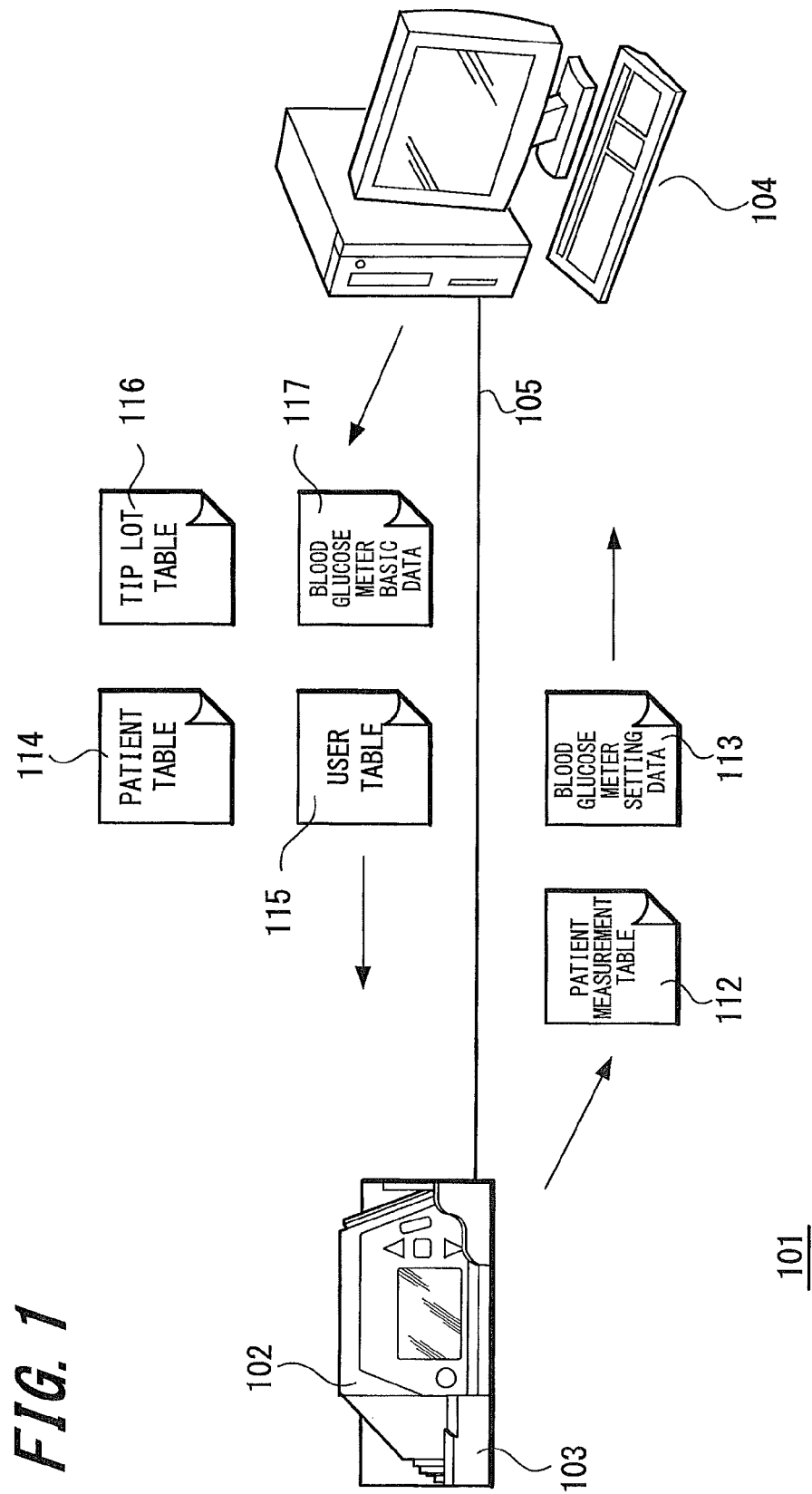
FIG. 1 is a schematic view showing the overall configuration of a blood glucose level managing system according to an embodiment of the present invention.

FIG. 1 is a schematic view showing the overall configuration of a blood glucose measuring system according to an example of the embodiments of the present invention.

A blood glucose measuring system 101 includes a blood glucose meter 102 (which is a blood glucose measuring device), a cradle 103 and a measurement data managing device 104.

The blood glucose meter 102 is a portable device that basically fits in the palm of an adult hand and that is operated using a secondary battery such as a lithium-ion secondary battery.

In the case where the blood glucose level of a patient is measured by a doctor, a nurse or the like, generally the blood glucose meter 102 is brought into a ward of a hospital, and a tiny amount of blood is drawn from the patent to measure the blood glucose level.

Make sure that the blood glucose meter 102 is mounted on the cradle 103 after performing the blood glucose measurement and insulin administration.

In addition to charging the battery of the blood glucose meter 102, the cradle 103 also functions as an interface through which the blood glucose meter 102 transmits/receives data to/from the measurement data managing device 104.

The partner to/from which the blood glucose meter 102 transmits/receives data through the cradle 103 is the measurement data managing device 104.

The measurement data managing device 104, which is configured by a personal computer, is connected with the cradle 103 through a USB cable 105.

A known OS operates to execute the measurement data managing device 104. Further, a program for causing the computer to function as the measurement data managing device 104 operates under the OS.

As soon as the blood glucose meter 102 is mounted on the cradle 103, the communication between the blood glucose meter 102 and the measurement data managing device 104 is performed through the cradle 103. At this time, if there is a patient measurement table 112 in the blood glucose meter 102, the measurement data stored in the patient measurement table 112 will be transmitted to the measurement data managing device 104 immediately.

Further, by transmitting a predetermined command from the measurement data managing device 104, blood glucose meter setting data 113 can be downloaded from the blood glucose meter 102 to the measurement data managing device 104.

Further, a patient table 114, a user table 115, a tip lot table 116 and blood glucose meter basic data 117 can be uploaded to the blood glucose meter 102 from the measurement data managing device 104.

The details about these data will be described later.

[Appearance: Blood Glucose Meter 102]

Figure 2A:
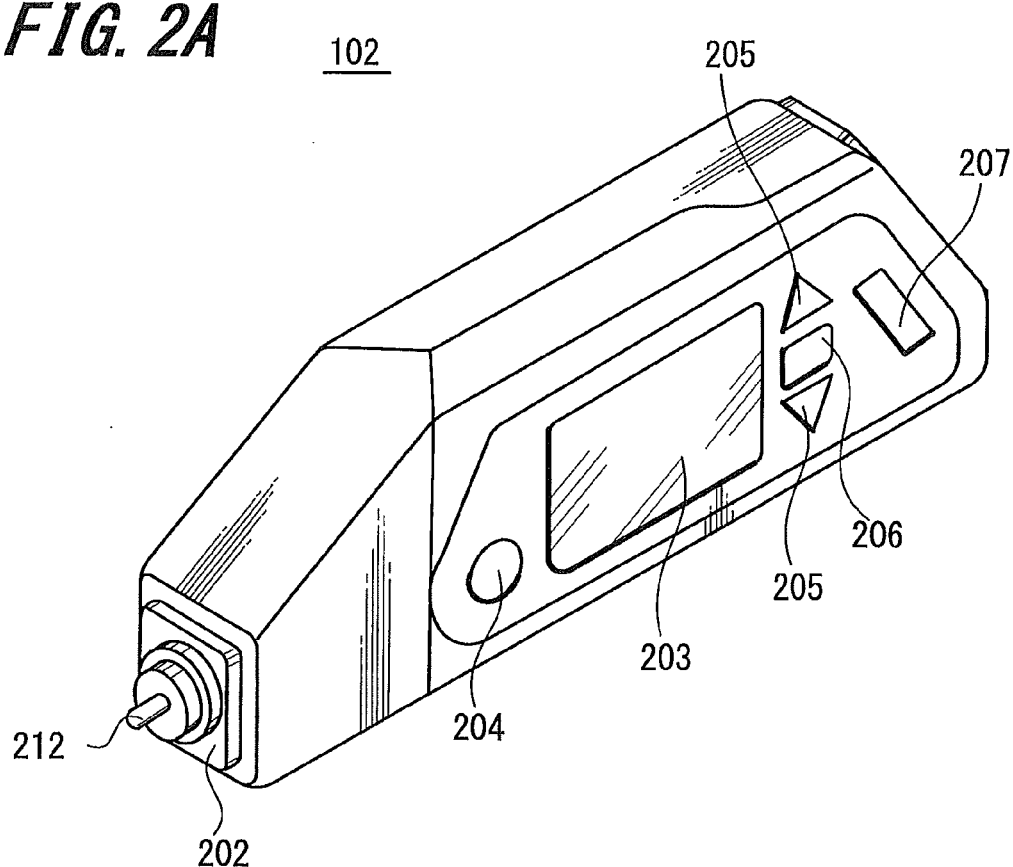
FIGS. 2A and 2B are perspective views showing the appearance of a blood glucose meter.
Figure 2B:
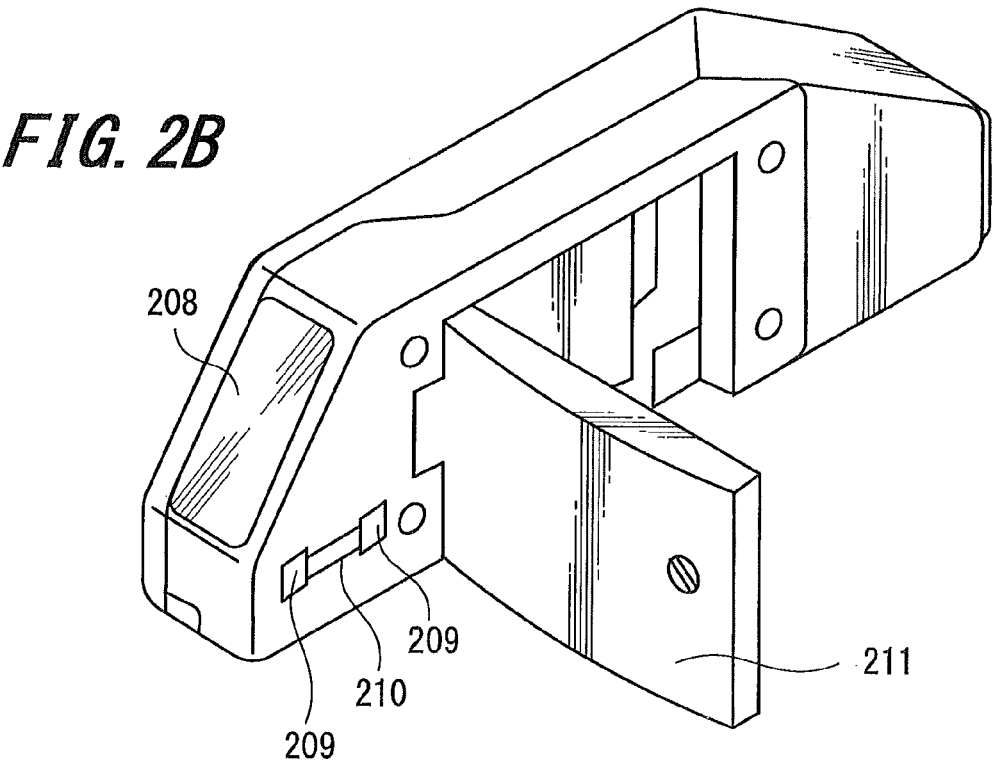

FIGS. 2A and 2B are perspective views showing the appearance of the blood glucose meter 102.

FIGS. 3A, 3B, 3C and 3D are views showing the blood glucose meter 102 when viewed from four directions.

Figure 3D:
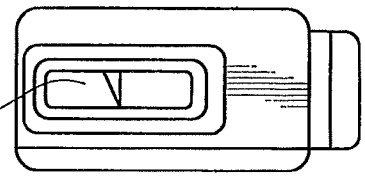
FIGS. 3A, 3B, 3C and 3D are views showing the blood glucose meter when viewed from four directions.
Figure 3B:
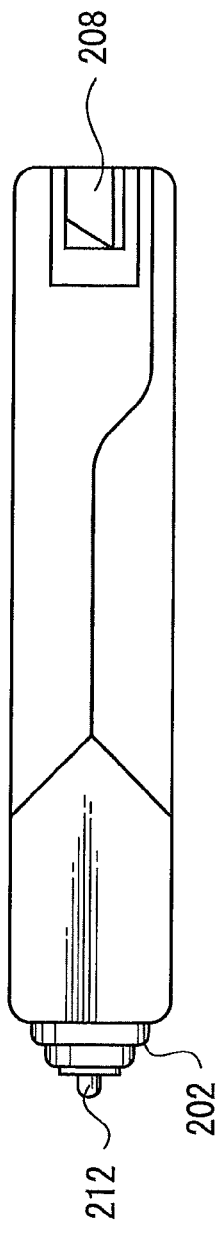
Figure 3A:
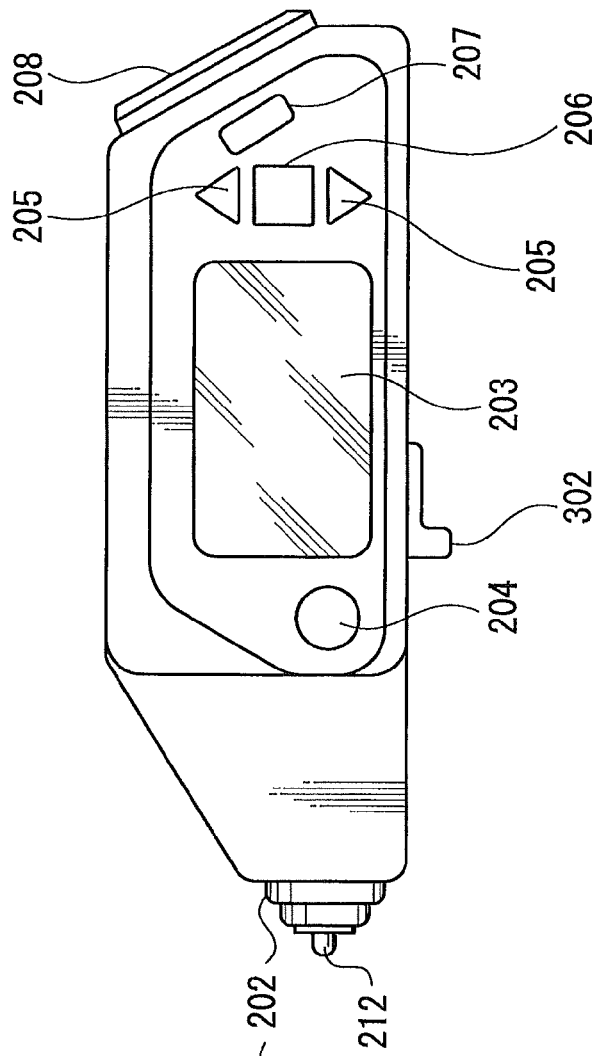
Figure 3C:
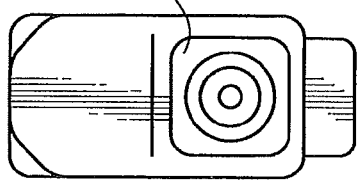

In order to facilitate description, the surface where an LCD is provided (as shown in FIGS. 2A and 3A) is referred to as a "body front surface" hereinafter, and the surface where a battery lid is provided (as shown in FIG. 2B) is referred to as a "body rear surface".

As shown in FIGS. 3A and 3B, an optical measuring section 202 is provided at the tip end of the blood glucose meter 102.

The optical measuring section 202 has a shape allowing a blood glucose measuring tip 212 (referred to as "measuring tip 212" hereinafter) to be attached and detached. The used measuring tip 212 can be detached from the optical measuring section 202 by operating an eject lever 302.

As shown in FIG. 2A and FIG. 3A, a power switch 204, Cursor keys 205, an Enter key 206 and a bar-code key 207 are arranged on the side surface (the body front surface) where the LCD 203 (a liquid crystal display) is provided, at positions beside the LCD 203.

The power switch 204 is used to switch on and off the power of the blood glucose meter 102.

The Cursor keys 205 are used to move the cursor to select one of a plurality of items displayed on the LCD 203.

The Enter key 206 is used to issue an instruction for "executing" or "selecting" the item selected by the cursor.

The bar-code key 207 is used to cause a bar-code reader 208 shown in FIG. 3D to operate, wherein the bar-code reader 208 is arranged on a side of the blood glucose meter 102 opposite to the side where the optical measuring section 202 is arranged.

The bar-code reader 208 is a bar-code reading device configured by a combination of a known red laser diode and a light-receiving element such as a phototransistor. Incidentally, an image sensor such as a CCD, a CMOS or the like can be used instead of the light-receiving element.

The basic mechanism of the blood glucose meter 102 for measuring blood glucose is identical to that of the conventional arts, and will be briefly described below. The measuring tip 212 is attached to the optical measuring section 202, the fingertip of the patient is stuck with a puncture tool, and the blood exuded from the fingertip is soaked into the measuring tip 212. A test paper made of a porous membrane such as a polyethersulfone membrane is provided inside the measuring tip 212. Further, when the blood soaked into the measuring tip 212 is permeated into the test paper, the blood will be reacted with the reagent contained in the test paper, so that the test paper develops a color. The color reaction requires about several to ten and several seconds, and the reaction time is affected by the ambient temperature.

After a predetermined reaction time has elapsed, a light-emitting element is caused to emit light, the light emitted from the light-emitting element irradiates to the test paper, and the light reflected from the test paper is received by the light-receiving element. Further, an analog light-receiving intensity signal obtained from the light-receiving element is converted into a digital value, and thereafter the digital value is converted into the blood glucose level to be displayed on the LCD 203.

Incidentally, the mechanism of blood glucose measurement on the side of the blood glucose meter 102 is not limited to the aforesaid optical measurement method in which a coloring reagent is used, but may be any other methods possible be used to perform the conventional blood glucose measurement, such as an electrochemical sensor method or the like.

As shown in FIG. 2B, a power terminal 209 and an infrared communication window 210 are provided in the body rear surface on the side of the bar-code reader 208. When the blood glucose meter 102 is mounted on the cradle 103, the power terminal 209 is brought into contact with a charging terminal 402 (see FIGS. 4A and 4B) provided in the cradle 103, so that the blood glucose meter 102 is charged while an infrared communication between the blood glucose meter 102 and the cradle 103 is performed. Incidentally, the battery lid 211 is also provided on the body rear surface.

[Appearance: Cradle 103]

Figure 4A:
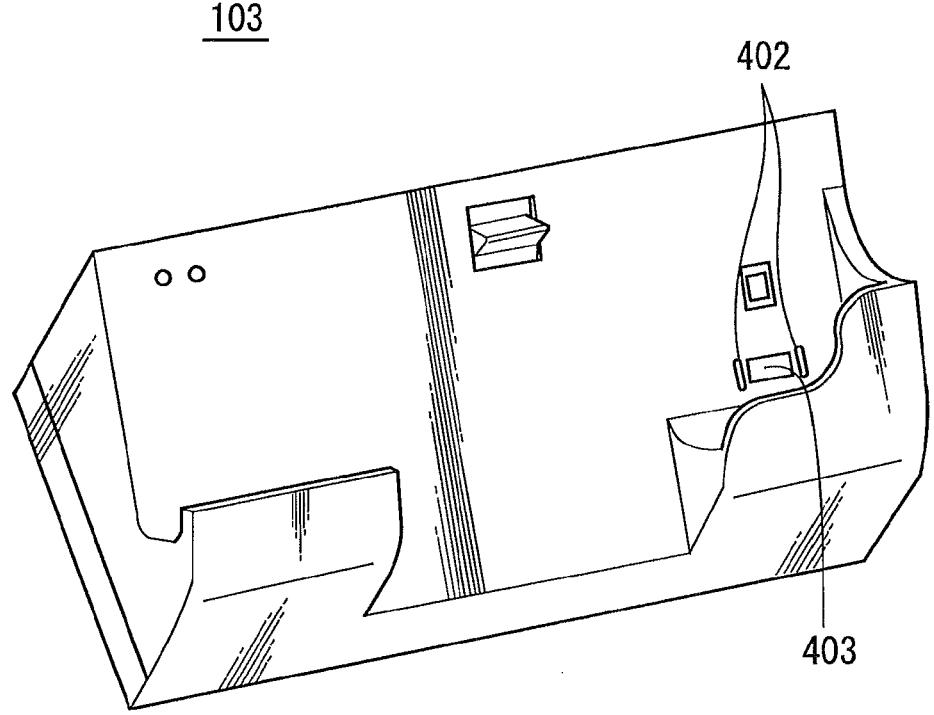
FIGS. 4A and 4B are views showing the appearance of a cradle in a state when the blood glucose meter is removed therefrom.
Figure 4B:
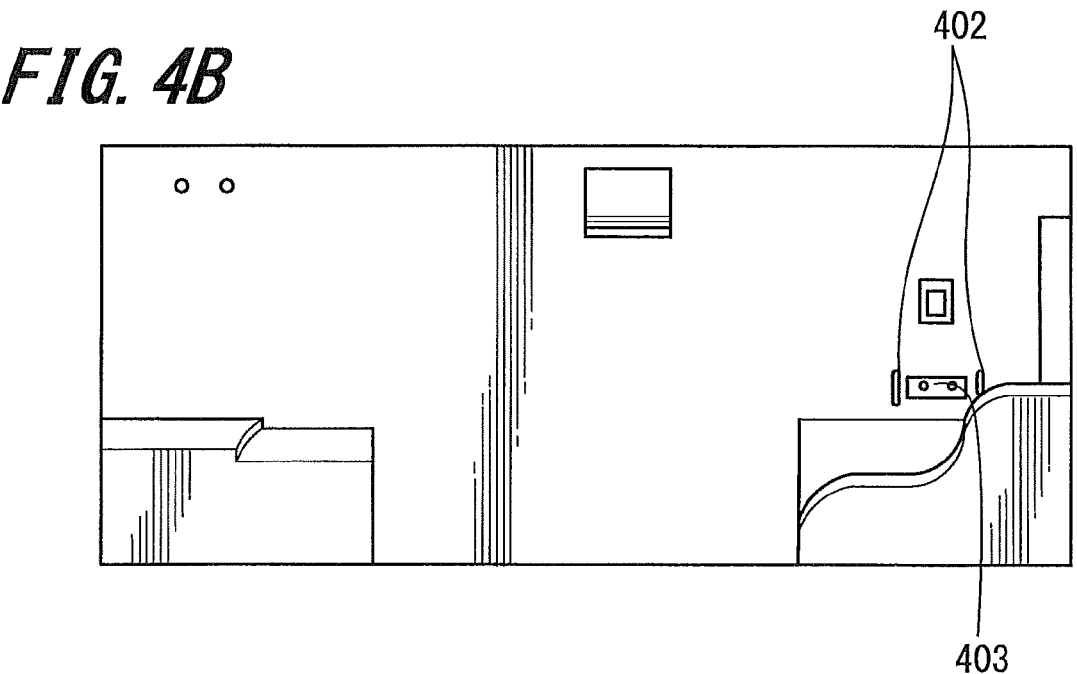
Figure 5A:
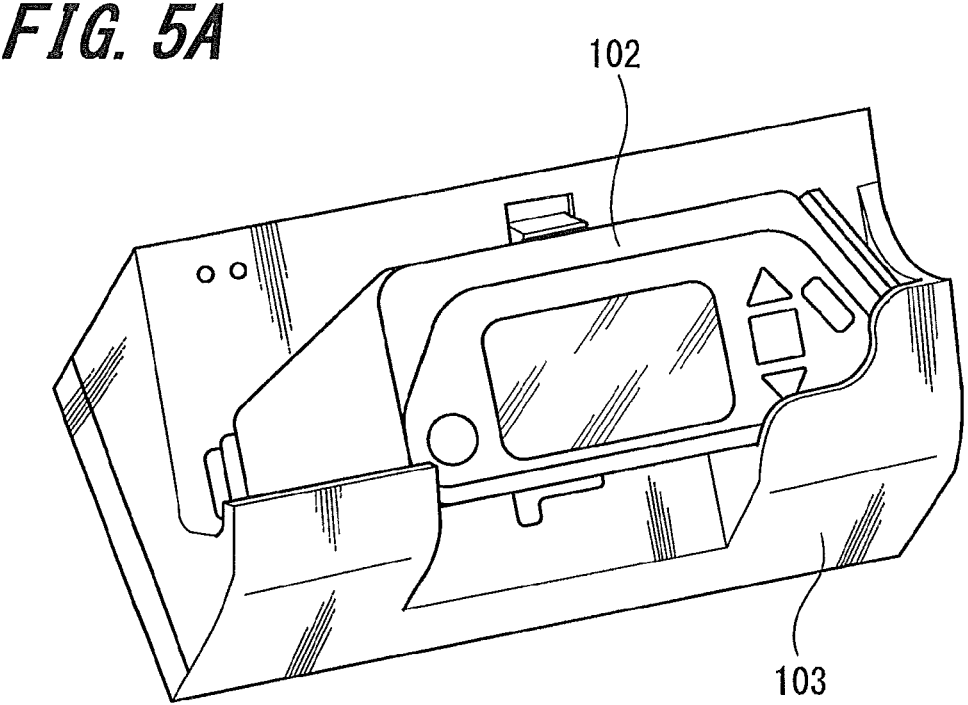
FIGS. 5A and 5B are views showing the appearance of the cradle in a state when the blood glucose meter is mounted thereon.
Figure 5B:
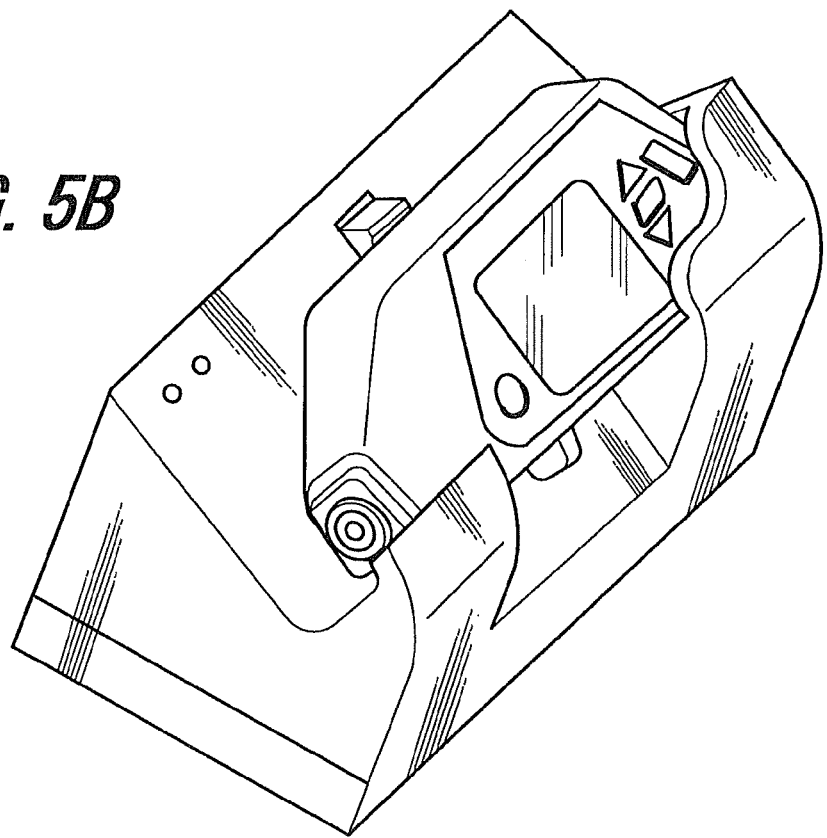

FIGS. 4A and 4B are views showing the appearance of the cradle 103 in a state when the blood glucose meter 102 is removed therefrom, and FIGS. 5A and 5B are views showing the appearance of the cradle 103 in a state when the blood glucose meter 102 is mounted thereon.

As shown in FIGS. 4A and 4B, the charging terminal 402 is arranged in the cradle 103 at a position corresponding to the power terminal 209 of the blood glucose meter 102. Similarly, an infrared communication window 403 is arranged in the cradle 103 at a position corresponding to the infrared communication window 210 of the blood glucose meter 102.

An infrared light-emitting diode and a phototransistor are provided inside both the infrared communication window 210 of the blood glucose meter 102 and the infrared communication window 403 of the cradle 103. These components constitute a known IrDA (Infrared Data Association) based infrared serial communication interface.

As shown in FIG. 1, the cradle 103 is connected to the measurement data managing device 104 through the USB cable 105. The cradle 103 has a function of charging the battery of the blood glucose meter 102. Since it is possible to connect many cradles 103 to the measurement data managing device 104, the cradle 103 is configured as a self-powered device which does not receive power supply from a USB terminal of the measurement data managing device 104.

[Hardware: Blood Glucose Meter 102]

Figure 6:
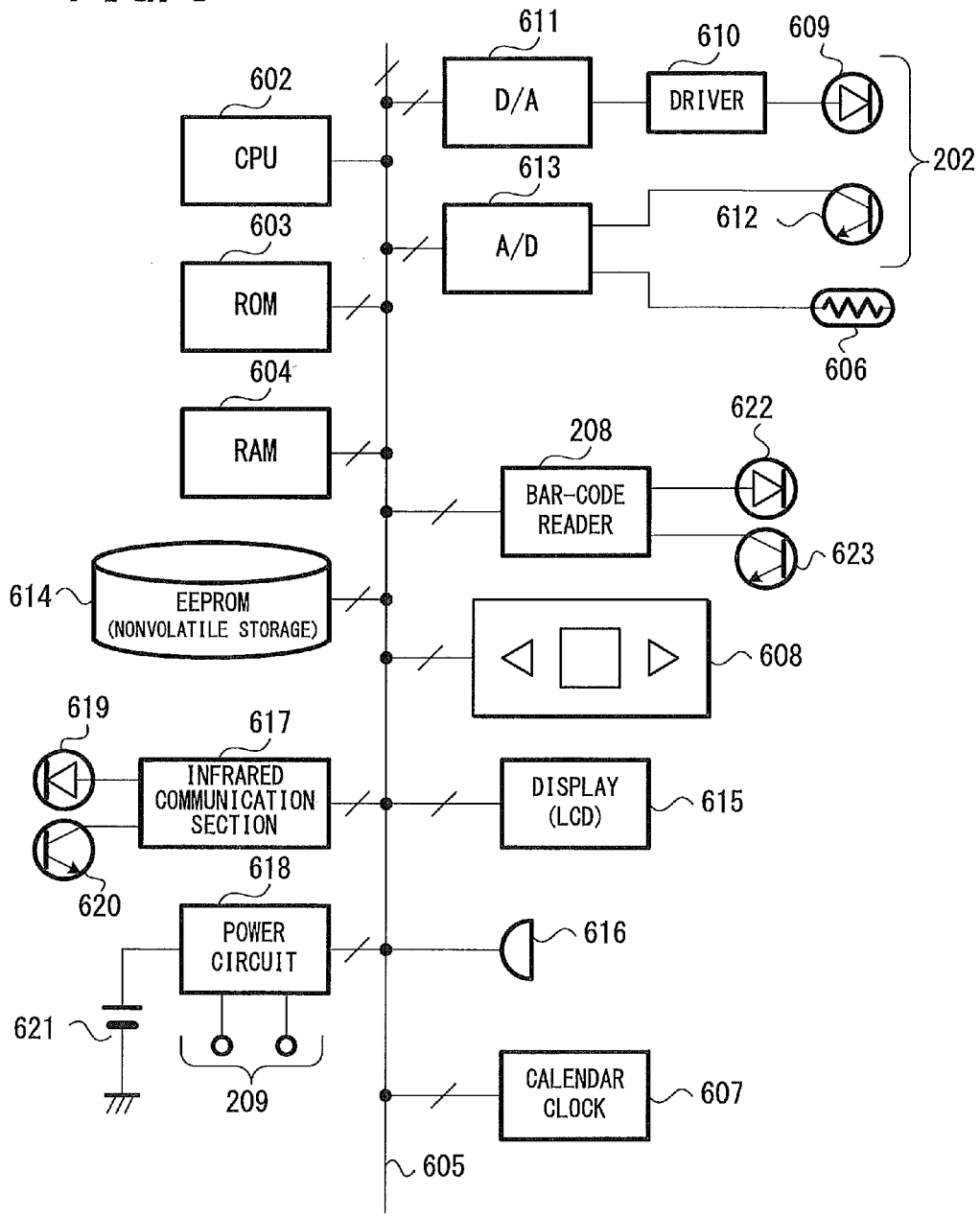
FIG. 6 is a block diagram showing the internal configuration of the blood glucose meter.

FIG. 6 is a block diagram showing the internal configuration of the blood glucose meter 102.

The blood glucose meter 102 includes a CPU 602, a ROM 603, a RAM 604, and a bus 605 for connecting the CPU 602, the ROM 603 and the RAM 604. In addition to the aforesaid components, a section for providing a data input function and a section for providing a data output function are also connected to the bus 605.

For sake of convenience, hereinafter the CPU 602, the ROM 603, the RAM 604 and the bus 605 are referred to as a microcomputer that constitutes the blood glucose meter 102.

The section for providing a data input function of the blood glucose meter 102 includes the optical measuring section 202 for obtaining blood glucose measurement data, a thermistor 606 for obtaining temperature data, the bar-code reader 208, a calendar clock 607, and an operating section 608.

The optical measuring section 202 includes a light-emitting portion and a light-receiving portion, wherein the light-emitting portion includes a light-emitting diode 609, a driver 610 of the light-emitting diode 609, and a D/A converter 611 connected to the driver 610, and the light-receiving portion includes a phototransistor 612 and an A/D converter 613.

Since the test paper arranged inside the measuring tip 212 needs to be irradiated by light of a suitable intensity, the light-emitting diode 609 is controlled so as to emit light based on light-emitting intensity data stored in a below-mentioned nonvolatile storage 614. In other words, the light-emitting intensity data is read out from the nonvolatile storage 614, converted into an analog voltage signal by the D/A converter 611, and then power-amplified by the driver 610 to drive the light-emitting diode 609 to emit light.

On the other hand, a signal voltage of intensity of the light received by the phototransistor 612 is converted into digital data by the A/D converter 613. Further, the converted digital data is converted into blood glucose level data by performing a predetermined arithmetic process executed by the CPU 602, and then the blood glucose level data is recorded in a predetermined area of the RAM 604 and a predetermined area of the nonvolatile storage 614.

Further, the blood glucose meter 102 has the thermistor 606, and ambient temperature of the blood glucose meter 102 can be measured based on the change of the resistance of the thermistor 606. Similar to the phototransistor 612, the resistance of the thermistor 606 is converted into digital data by the A/D converter 613, and the digital data is stored in a predetermined area of the RAM 604 and a predetermined area of the nonvolatile storage 614. Incidentally, since it is not necessary to simultaneously measure the light-receiving intensity and the temperature, the A/D converter 613 can be shared by the phototransistor 612 and the thermistor 606.

The bar-code reader 208 causes a red laser diode 622 to emit light, the reflected light is received by a phototransistor 623 so that the bar-code is read, and the data recorded on the bar-code is outputted to the bus 605.

The calendar clock 607 is a known IC also called as a "real-time clock" which provides a date and time data output function, and is mounted as standard on many microcomputers, personal computers and the like.

In the blood glucose meter 102 according to the present embodiment of the present invention, since it is necessary to acquire information regarding the date and time when the blood glucose was being measured, date and time information is important information. In other words, the data to be collected and the date and time information have very close relation with each other. Further, the date and time information when the blood glucose was being measured needs to be stored in the patient measurement table 112 along with the blood glucose level. For this reason, the calendar clock 607 is daringly shown in the drawings.

The operating section 608 is a known key switch formed by push-buttons, the operating section 608 including the Cursor keys 205 and the Enter key 206. The operating section 608 is used for a user to operate the blood glucose meter 102 according to the content displayed on a below-mentioned display 615 which is a LCD.

The section for providing a data output function of the blood glucose meter 102 includes the display 615 configured by the LCD 203, a buzzer 616 and an infrared communication section 617.

Various screens are displayed on the display 615 by a program stored in the ROM 603 and executed by the CPU 602. The details about these screens will be described later.

The buzzer 616 is mainly used to notify the user that the bar-code reader 208 has successfully read the bar-code, that the measurement operation of the blood glucose measurement has completed, that the infrared communication has completed, or that an error message is displayed. The buzzer

616 may also sound every time when operating the operating section 608 depending on setting.

As mentioned above, an infrared light-emitting diode 619 and a phototransistor 620 are connected to the infrared communication section 617, and these components constitute an IrDA based serial interface. When detecting that the blood glucose meter 102 has received power supply from the cradle 103 based on voltage changing of the power terminal 209, a power circuit 618 reports this fact to the CPU 602 through the bus 605. Further, based on the control of the CPU 602, the infrared communication function of the infrared communication section 617 is started, so that the infrared communication between the blood sugar meter 102 and the cradle 103 is performed, and thereby the various tables stored in the nonvolatile storage 614 transmits/receives data to/from the measurement data managing device 104 and is updated.

In other words, when performing the infrared communication between the blood glucose meter 102 and the cradle 103, the infrared communication is immediately executed as soon as the blood glucose meter 102 is mounted on the cradle 103 without needing to operate the operating section 608 and the like of the blood glucose meter 102.

In addition to the data output function, the blood glucose meter 102 is provided with the nonvolatile storage 614 (which is an EEPROM) that provides data storage function. The patient table 114, the user table 115, the tip lot table 116, the patient measurement table 112, the blood glucose meter setting data 113 and the like are stored in the nonvolatile storage 614. These data are updated when the communication between the blood glucose meter 102 and the measurement data managing device 104 is performed through the cradle 103. Incidentally, a flash memory may also be used instead of the EEPROM.

[Hardware: Cradle 103]

Figure 7:
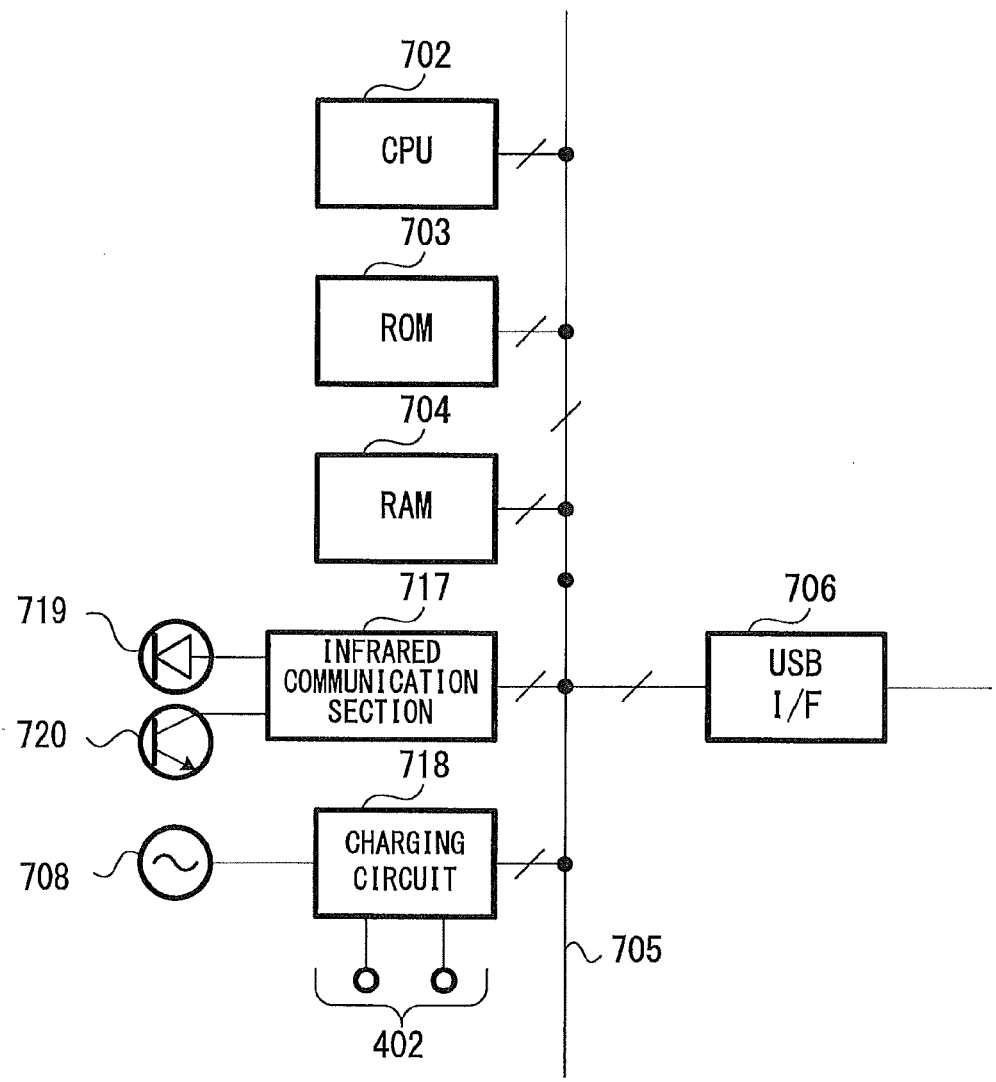
FIG. 7 is a block diagram showing the internal configuration of the cradle.

FIG. 7 is a block diagram showing the internal configuration of the cradle 103.

Figure 8:
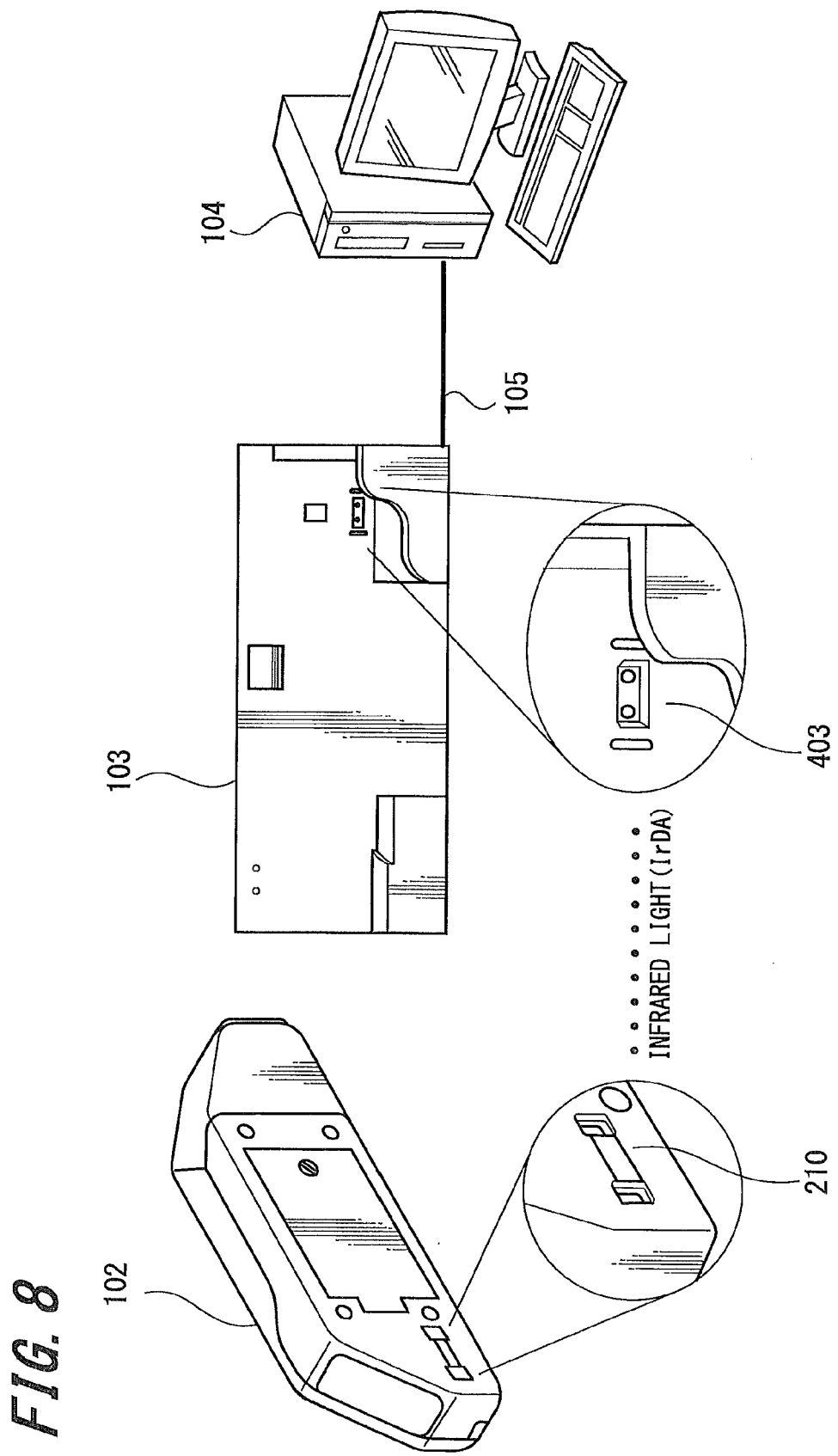
FIG. 8 is a block diagram showing connection state of the blood glucose meter, the cradle and a measurement data managing device.

FIG. 8 is a view schematically showing connection state of the blood glucose meter 102, the cradle 103 and the measurement data managing device 104.

As shown in FIG. 7, the cradle 103 includes a CPU 702, a ROM 703, a RAM 704, an infrared communication section 717, a USB interface (I/F) 706, a charging circuit 718 and a bus 705 which connects these components, wherein the CPU 702, the ROM 703 and the RAM 704 constitute a microcomputer, and the infrared communication section 717 has an infrared light-emitting diode 719 and a phototransistor 720 connected thereto.

When detecting that the blood glucose meter 102, which is a load, is connected based on voltage changing of the charging terminal 402, the charging circuit 718 reports this fact to the CPU 702 through the bus 705. Further, based on the control of the CPU 702, the infrared communication function of the infrared communication section 717 is started, so that the communication between the blood glucose meter 102 and the measurement data managing device 104 is performed through the infrared communication section 717 and the USB interface 706.

As described above, the blood glucose meter 102 and the cradle 103 are connected with each other through the IrDA, and the cradle 103 and the measurement data managing device 104 are connected with each other through the USB. From this aspect, the cradle 103 serves as an interface to enable data communication between the measurement data managing device 104 and the blood glucose meter 102.

[Hardware: Measurement Data Managing Device 104]

Figure 9:
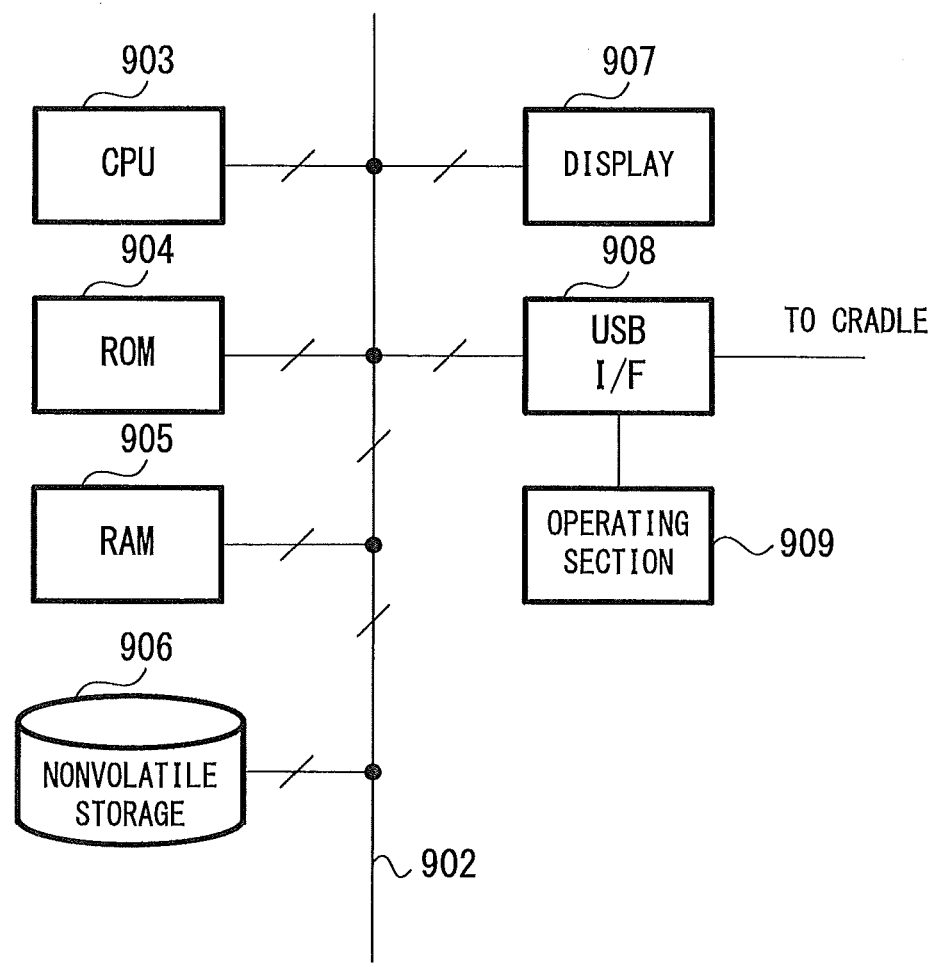
FIG. 9 is a block diagram showing the measurement data managing device.

FIG. 9 is a block diagram showing the measurement data managing device 104.

As described above, the measurement data managing device 104 is actually a known personal computer.

A bus 902 is provided inside the measurement data managing device 104. A CPU 903, a ROM 904, a RAM 905, a nonvolatile storage (such as a hard disk device or the like) 906, a display (such as a LCD or the like) 907 and a USB interface (I/F) 908 are connected to the bus 902. In addition to an operating section (such as a keyboard, a mouse and/or the like) 909, the cradle 103 is connected to the USB interface 908.

[Blood Glucose Measurement Procedure of Blood Glucose Meter 102]

The flow of a blood glucose measurement procedure with the blood glucose meter 102 will be described below with reference to FIG. 10.

Figure 10:
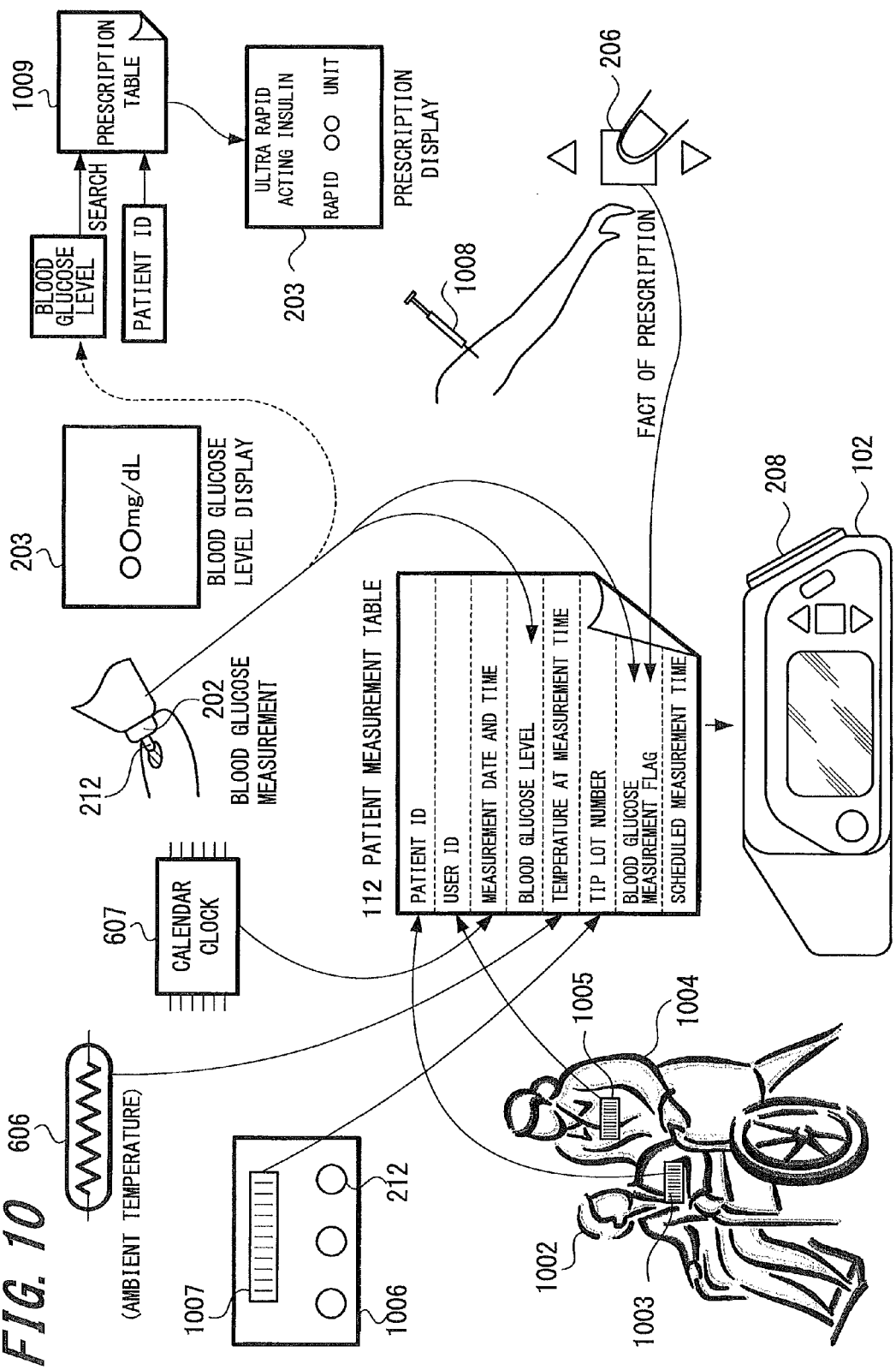
FIG. 10 is a view schematically showing the flow of a blood glucose measurement procedure with the blood glucose meter.

FIG. 10 is a view schematically showing the flow of the blood glucose measurement procedure with the blood glucose meter 102.

(1) A patient ID 1003, which is a bar-code indicated in a name tag or the like of a patient 1002, is read by the bar-code reader 208.

The read patient ID 1003 is first used as a search key for searching the patient table 114. Specifically, the patient ID 1003 is used as a search key to search the patient table 114 previously transmitted from the measurement data managing device 104 and stored in the nonvolatile storage 614. Further, scheduled blood glucose measurement time recorded in a record of the patient 1002 is read out. As a new record of the patient measurement table 112, the patient ID 1003 and the scheduled blood glucose measurement time obtained in such a manner are respectively additionally recorded in a "PATIENT ID" field and a "SCHEDULED BLOOD GLUCOSE MEASUREMENT TIME" field.

(2) A user ID 1005, which is a bar-code indicated in a name tag or the like of a nurse 1004, is read by the bar-code reader 208.

Verification is performed to see whether or not the read user ID 1005 is included in the user table 115. The user table 115 is searched using the user ID as a search key, and if there is the user ID, a "USER ID" field of the record previously additionally recorded in the patient measurement table 112 will be overwritten by the user ID.

(3) A tip lot number 1007, which is a bar-code printed in a box 1006 of the measuring tip 212, is read by the bar-code reader 208.

Verification is performed to see whether or not the read tip lot number is included in the tip lot table 116. The tip lot table 116 is searched using the tip lot number as a search key, and if there is the tip lot number, a "TIP LOT NUMBER" field of the record previously additionally recorded in the patient measurement table 112 will be overwritten by the tip lot number.

(4) Immediately after recording the tip lot number in the "TIP LOT NUMBER" field of the patient measurement table 112 in (3), the ambient temperature is measured by the thermistor 606. Further, if it is judged that the ambient temperature is in a predetermined range, a "TEMPERATURE AT MEASUREMENT TIME" field of the record previously additionally recorded in the patient measurement table 112 will be overwritten by the ambient temperature.

(5) The measuring tip 212 is attached to the optical measuring section of the blood glucose meter 102 to measure the blood glucose. Further, the date and time data at measurement time is obtained from the calendar clock 607.

The "BLOOD GLUCOSE LEVEL" field of the record previously additionally recorded in the patient measurement table 112 is overwritten by the measured blood glucose level.

The "MEASUREMENT DATE AND TIME" field of the record previously additionally recorded in the patient measurement table 112 is overwritten by the date and time data.

A flag representing the fact that "the blood glucose has been measured" is recorded in a "BLOOD GLUCOSE MEASUREMENT FLAG" field.

Thereafter, the measured blood glucose level is displayed on the LCD 203 (the display 615).

(6) A prescription table 1009 of the patient is searched with the previously obtained patient ID 1003 and the blood glucose level, and kind and dosage of the drug (such as insulin and/or the like) prescribed for the patient 1002 are displayed on the LCD 203. Incidentally, the prescription table 1009 is stored in the patient table 114 for each patient ID.

(7) Following the prescription displayed on the LCD 203, the nurse 1004 administers the insulin and/or the like with a syringe 1008, and then inputs such a fact with the Enter key 206. As a result, a flag representing the fact that "prescription has been performed" is recorded in the "BLOOD GLUCOSE MEASUREMENT FLAG" field.

By performing the aforesaid measurement operation, the following contents are recorded in the patient measurement table 112:

Which user
has (or has not) measured blood glucose
for which patient
with respect to what scheduled measurement time
using a tip of what tip lot number
at what ambient temperature
what is the blood glucose level (if blood glucose has been measured)
what is the measurement date and time (if blood glucose has been measured)
whether or not insulin and/or the like has been prescribed.

The blood glucose measurement operation and the insulin prescription operation are generally performed at a predetermined time after the patient having meal. Further, the blood glucose measurement procedure and the insulin prescription procedure may also be performed at a predetermined time before the patient having meal. The blood glucose measurement procedure and insulin prescription procedure are collectively performed for a plurality of patients at a predetermined time.

The work unit of the blood glucose measurement operation and/or the insulin prescription operation collectively performed for a plurality of patients at a predetermined time is "round". For example, the expression of "one round in 30 minutes after breakfast" and the like are used in practice.

In order to prevent mistake in the blood glucose measurement procedure, the insulin prescription procedure and the like, the measurement data managing device 104 only transmits data for performing one round to the blood glucose meter 102. Such data are the patient table 114, the user table 115, and the tip lot table 116.

Further, make sure that the blood glucose meter 102 is mounted on the cradle 103 after the round is completed. the patient measurement table 112 is transmitted from the blood glucose meter 102 to the measurement data managing device 104 as soon as the blood glucose meter 102 is mounted on the cradle 103. The measurement data managing device 104 records the patient measurement table 112 in the tables inside thereof.

[Nickname Managing Function of Measurement Data Managing Device 104]

Nickname function performed by the measurement data managing device 104 will be described below with reference to FIG. 11.

Figure 11:
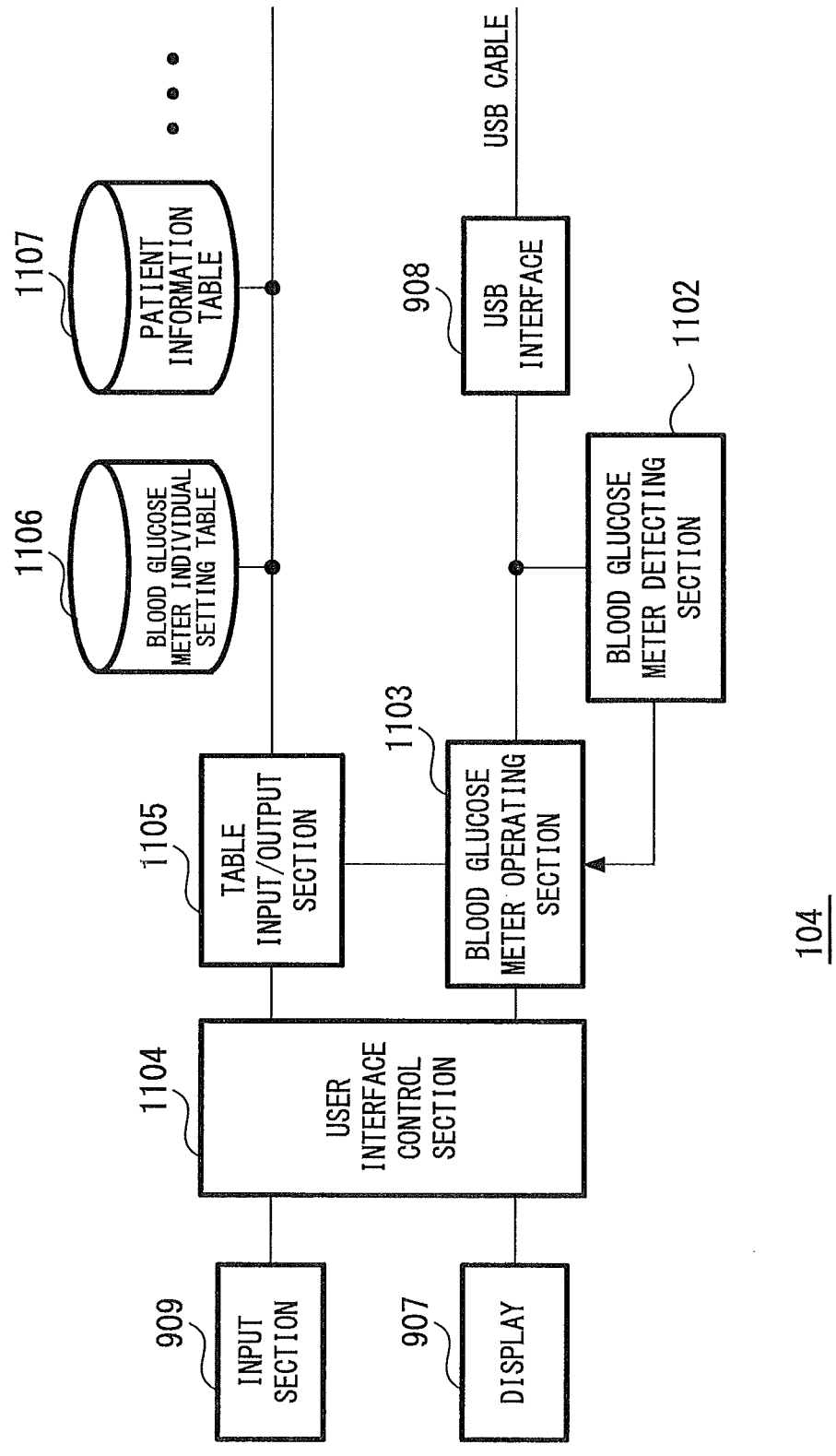
FIG. 11 is a functional block diagram of the measurement data managing device.

FIG. 11 is a functional block diagram of the measurement data managing device. Note that, in the present embodiment, only the function of the measurement data managing device 104 associated with the nickname will be described, although the measurement data managing device 104 also has various other functions not included in the disclosure of the present embodiment.

A blood glucose meter detecting section 1102 constantly monitors whether or not the blood glucose meter 102 is mounted on the cradle 103 through the USB interface 908. When the blood glucose meter 102 is mounted on the cradle 103 or when the blood glucose meter 102 is removed from the cradle 103, the blood glucose meter detecting section 1102 reports such fact to a blood glucose meter operating section 1103.

The blood glucose meter detecting section 1102 provides a function of detecting the establishment of the communication between the measurement data managing device 104 and the blood glucose meter 102. The details of this function of the blood glucose meter detecting section 1102 will be described later with reference to FIG. 25.

The blood glucose meter operating section 1103 mainly performs the following two operations.

One is essential data communication operation performed immediately after the blood glucose meter detecting section 1102 reports that the blood glucose meter 102 is mounted on the cradle 103. The essential data communication operation is performed basically without making any inquiry to the user.

The other is optional data communication operation for transmitting necessary data to the blood glucose meter 102 for it to perform round. The optional data communication operation is performed in response to the operation performed by the user.

In other words, basically the operation for the measurement data managing device 104 to collect the data from the blood glucose meter 102 is performed automatically as soon as the blood glucose meter 102 is mounted on the cradle 103.

On the other hand, the operation for the measurement data managing device 104 to transmit the data to the blood glucose meter 102 has to be performed in response to (manual) operation performed by the user.

The input section 909 is configured by a keyboard, a mouse and/or the like. The display 907 is an LCD or the like. The input section 909 and the display 907 are connected to a user interface control section 1104.

The user interface control section 1104 makes the display 907 to display a predetermined operation screen. Further, when receiving user's operation from the input section 909, the user interface control section 1104 changes the operation screen displayed on the display 907, sends a predetermined instruction to the blood glucose meter detecting section 1102, and inputs/outputs necessary data to/from a table input/output section 1105.

The table input/output section 1105 is an interface for performing data input/output operation between many tables stored in the nonvolatile storage of the measurement data managing device 104 (such as a blood glucose meter individual setting table 1106, a patient information table 1107 and the like), the user interface control section 1104 and the blood glucose meter operating section 1103. To be specific, the table input/output section 1105 is a database manager called "middleware".

The measurement data managing device 104 needs to store large amounts of data therein. Particularly, since the patient measurement table 112 is downloaded from the blood glucose meter 102 and stored in the nonvolatile storage every time when round is completed, volumes of data will increase day by day. To cope with the large amounts of data and achieve quick data input/output function, it is preferred to employ the middleware. Further, by employing the middleware, efficiency of program construction can be improved.

Note that, although only the blood glucose meter individual setting table 1106 and the patient information table 1107 are shown in FIG. 11, there are actually more tables. In FIG. 11, the tables unnecessary for describing the present embodiment are omitted.

FIG. 12 is a view showing each field of the blood glucose meter individual setting table 1106.

The blood glucose meter individual setting table 1106 includes a "SERIAL NUMBER" field, a "NICKNAME" field and a "VARIOUS SET VALUES" field. As inferred by the name "blood glucose meter individual setting table", the values of these fields are set for each blood glucose meter 102, and are recorded using a serial number as a key. Incidentally, the serial number is a unique number assigned for the blood glucose meter 102 when the blood glucose meter 102 is shipped from the factory.

The measurement data managing device 104 registers the serial number of the blood glucose meter 102 handled thereby in the blood glucose meter individual setting table 1106. In order to distinguish a plurality of blood glucose meters 102 from each other, the user creates a nickname for each registered blood glucose meter 102. The created nickname is recorded in the blood glucose meter individual setting table 1106, as well as recorded in the blood glucose meter 102.

Figure 19:
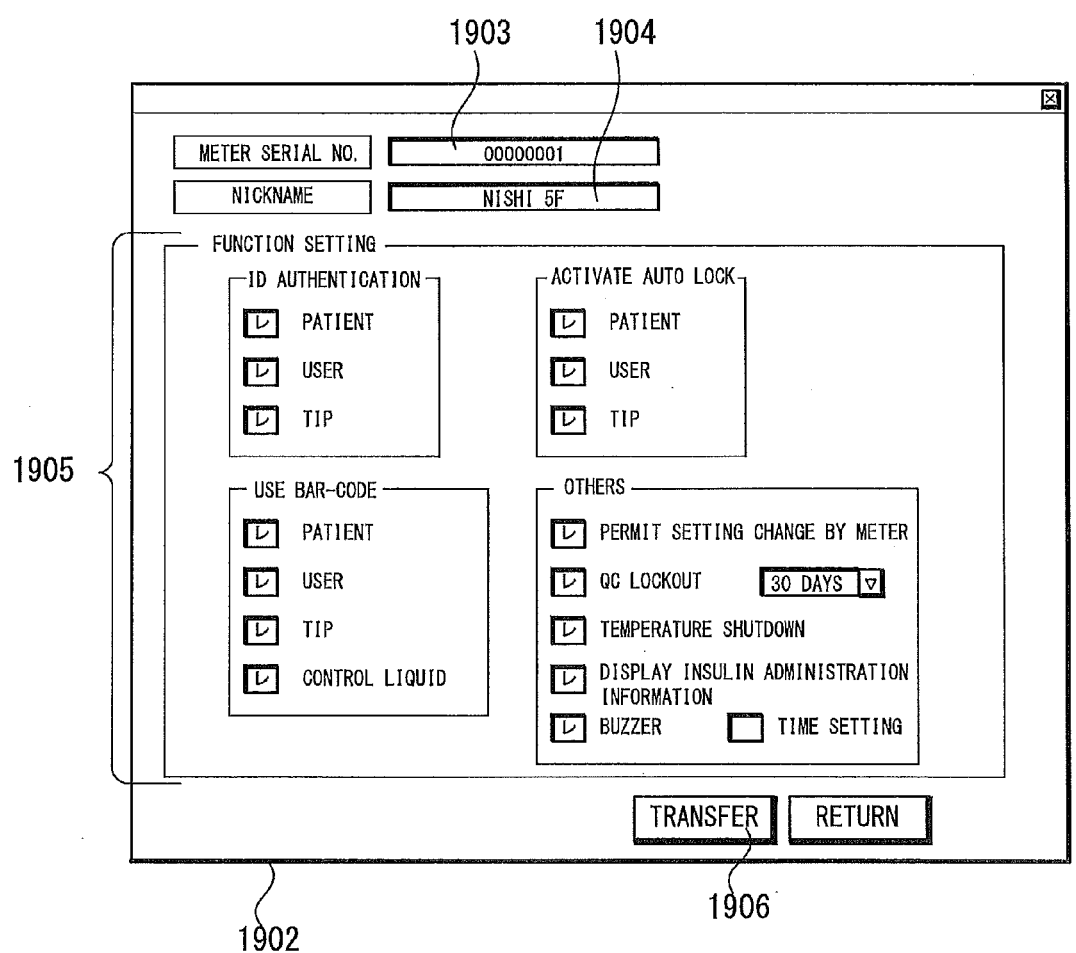
FIG. 19 is a view showing a meter setting transfer window.

When pressing a "TRANSFER METER SETTING" button (which is to be described later with reference to FIG. 16) to display a meter setting transfer window, the content of the various set values recorded in the blood glucose meter individual setting table 1106 will be displayed in the meter setting transfer window as shown in FIG. 19. Further, in the meter setting transfer window, set values (including the nickname) can be changed.

Figure 13:
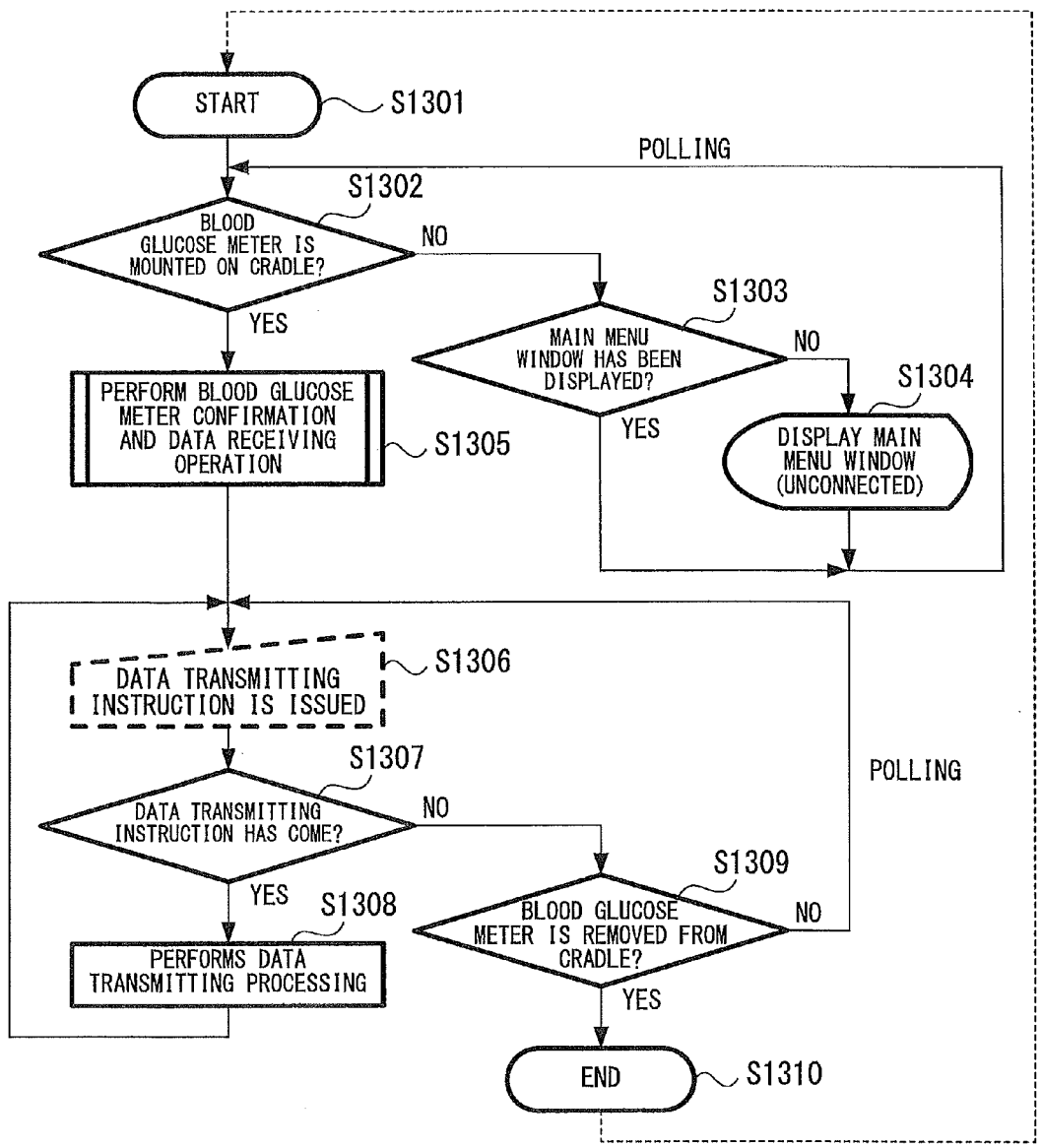
FIG. 13 is a flowchart showing the operation flow of the measurement data managing device.

FIG. 13 is a flowchart showing the operation flow of the measurement data managing device 104.

When the processing is started (Step S1301), the blood glucose meter detecting section 1102 confirms whether or not the blood glucose meter 102 is mounted on the cradle 103 through the USB interface 908 (Step S1302). If it is confirmed that there is no blood glucose meter 102, the blood glucose meter detecting section 1102 will perform a confirmation on the user interface control section 1104 to see whether or not a main menu window has been displayed (Step S1303).

If it is confirmed that the main menu window has not been displayed yet ("NO" in Step S1303), the user interface control section 1104 will display a main menu window which shows a state where the blood glucose meter 102 is not connected (Step S1304). Further, the blood glucose meter detecting section 1102 repeats the operation of confirming the existence of the blood glucose meter 102 again (Step S1302).

If it is confirmed that the main menu window has been displayed ("YES" in Step S1303), the blood glucose meter detecting section 1102 will repeat the operation of confirming the existence of the blood glucose meter 102 again (Step S1302).

The polling between Step S1302 and Steps S1303 and S1304 is performed at an interval of about 100 msec.

If the blood glucose meter detecting section 1102 has confirmed the existence of the blood glucose meter 102 ("YES" in Step S1302), the blood glucose meter operating section 1103 will perform blood glucose meter confirmation and data receiving operation (Step S1305).

The following is a loop processing.

If a data transmitting instruction is issued from the user interface control section 1104 to the blood glucose meter operating section 1103 by operating the input section 909 by the user (Step S1306 and Step S1307), the blood glucose meter operating section 1103 performs a predetermined data transmitting processing (Step S1308).

If no data transmitting instruction is issued ("NO" in Step S1307), only processing of confirming the existence of the blood glucose meter 102 will be continued ("NO" in Step S1309, Step S1306, "NO" in Step S1307) as long as the blood glucose meter 102 is not removed from the cradle 103 ("NO" in Step S1309).

If the blood glucose meter detecting section 1102 detects that the blood glucose meter 102 is removed from the cradle 103 ("YES" in Step S1309), the processing will be once terminated (Step S1310). However, the processing is started again (Step S1301), the blood glucose meter detecting section 1102 confirms whether or not the blood glucose meter 102 is mounted on the cradle 103 through the USB interface 908 (Step S1302).

In other words, when the blood glucose meter 102 is not mounted on the cradle 103, the polling of Step S1302 and the polling of Step S1303 will be continued.

While when the blood glucose meter 102 is mounted on the cradle 103, the polling of Step S1309 will be continued (through Step S1306 and Step S1307).

Figure 14:
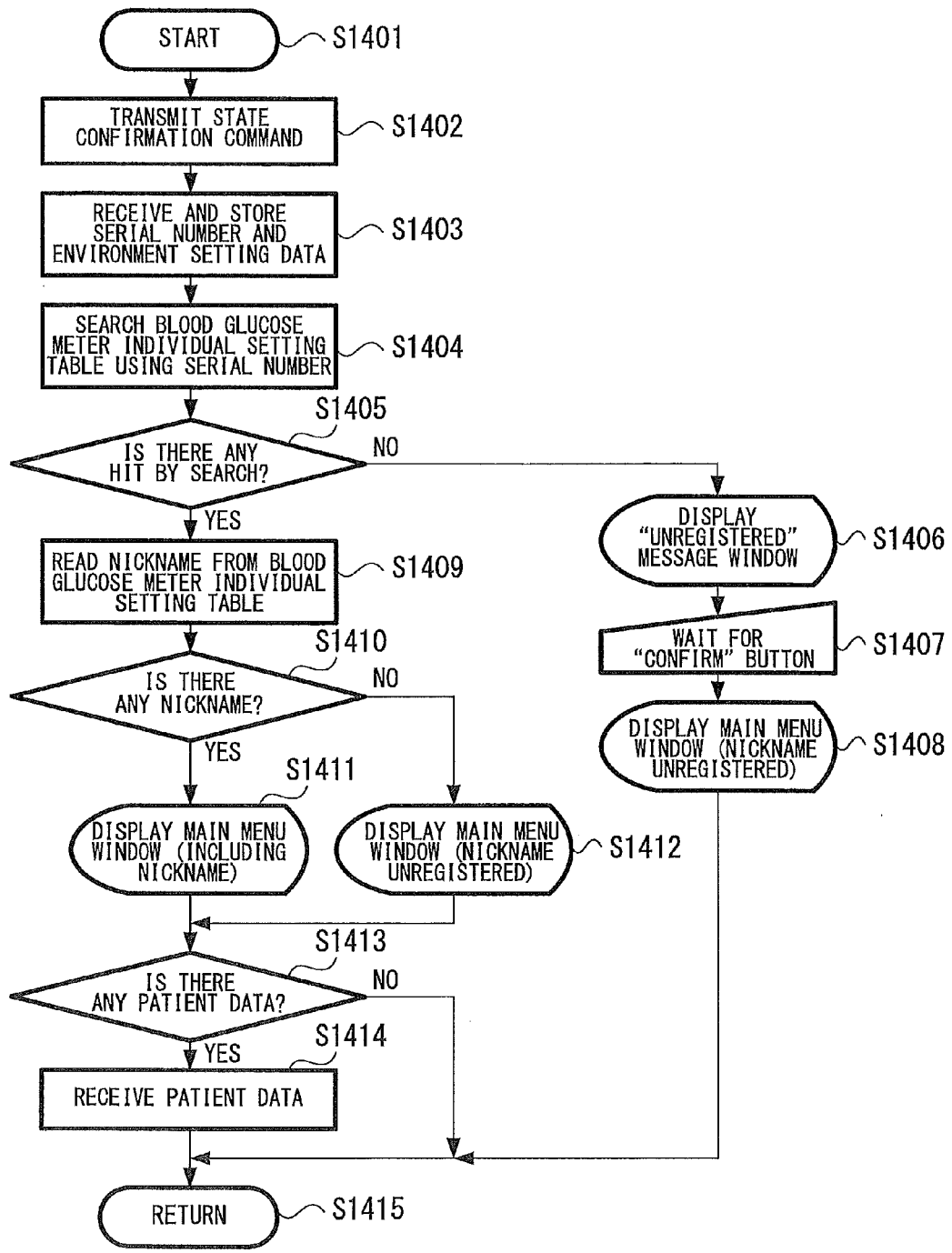
FIG. 14 is a flowchart showing operation of blood glucose meter confirmation and operation of data receiving processing.

FIG. 14 is a flowchart showing operation of blood glucose meter confirmation and operation of data receiving processing. FIG. 14 corresponds to the content of Step S1305 of FIG. 13.

When the processing is started (Step S1401), the blood glucose meter operating section 1103 transmits a "state confirmation command" to the blood glucose meter 102 through the USB interface 908 (Step S1402). As a result, the blood glucose meter setting data 113 shown in FIG. 1 is transmitted from the blood glucose meter 102 to the measurement data managing device 104. The blood glucose meter setting data 113 includes the serial number and environment setting data. The blood glucose meter operating section 1103 receives and stores the blood glucose meter setting data 113 (Step S1403).

Next, through the table input/output section 1105, the blood glucose meter operating section 1103 searches the blood glucose meter individual setting table 1106 using the serial number read from the blood glucose meter setting data 113 as a search key (Step S1404).

As a result of the search, if it is judged that there is no the serial number in the blood glucose meter individual setting table 1106 ("NO" in Step S1405), the blood glucose meter operating section 1103 will report the result that "there is no the serial number in the blood glucose meter individual setting table 1106" to the user interface control section 1104. The user interface control section 1104 displays an "UNREGISTERED" message window (Step S1406). A "CONFIRM" button is provided in this message window. Further, the user interface control section 1104 waits for pressing operation of the "CONFIRM" button (Step S1407).

When the "CONFIRM" button is pressed by the user, the user interface control section 1104 makes the display 907 to display a main menu window. The main menu window shows an illustration which tells that the blood glucose meter 102 is connected and an indication of "UNREGISTERED", instead of the nickname of the blood glucose meter 102 (Step S1408). And the processing is terminated (Step S1415).

In Step S1405, as a result of the search, if there is a hit, which means there is the serial number in the blood glucose meter individual setting table 1106 ("YES" in Step S1405), the blood glucose meter operating section 1103 will read the nickname from the blood glucose meter individual setting table 1106 through the table input/output section 1105, and transfer the result to the user interface control section 1104 (Step S1409). Next, the user interface control section 1104 confirms whether or not there is any character string in the nickname transferred from the blood glucose meter operating section 1103 (Step S1410).

If there is any effective character contained in the nickname ("YES" in Step S1410), the user interface control section 1104 will display a main menu window in which the nickname transferred from the blood glucose meter operating section 1103 is displayed (Step S1411). The main menu window includes an illustration which tells that the blood glucose meter 102 is connected and the nickname of the blood glucose meter 102.

If there is no character string in the nickname ("NO" in Step S1410), the user interface control section 1104 will display a main menu window in which the nickname transferred from the blood glucose meter operating section 1103 is displayed (Step S1412). The main menu window shows an illustration which tells that the blood glucose meter 102 is connected and an indication of "UNREGISTERED", instead of the nickname of the blood glucose meter 102.

Next, the blood glucose meter operating section 1103 transmits a "state confirmation command" to the blood glucose meter 102 through the USB interface 908 to query whether or not there is any patient data (Step S1413).

If there is a response "there is patient data" sent from the blood glucose meter 102 ("YES" in Step S1413), the patient data will be received (Step S1410), and the processing will be terminated (Step S1414).

If there is a response "there is no patient data" sent from the blood glucose meter 102 ("NO" in Step S1413), the processing will be terminated (Step S1414).

Figure 15:
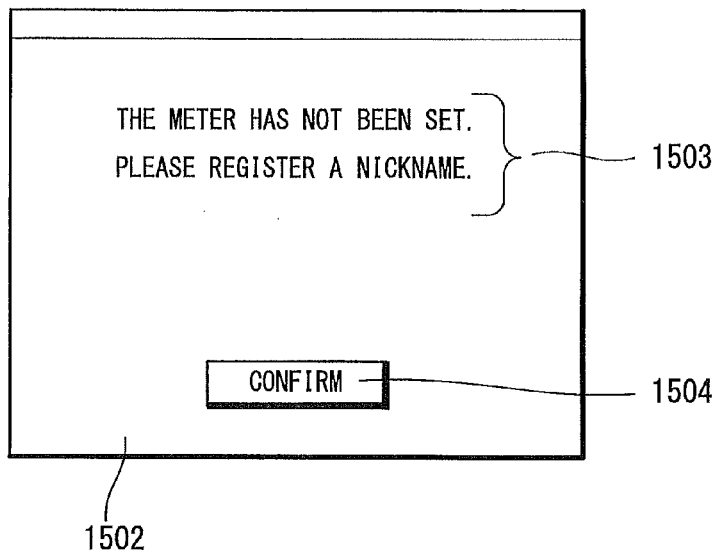
FIG. 15 is a view showing an "UNREGISTERED" message window.

FIG. 15 is a view showing the "UNREGISTERED" message window. The "UNREGISTERED" message window is displayed on the display 907 in Step S1406 of FIG. 14.

A message 1503 that is an instruction to the user is displayed in an "UNREGISTERED" message window 1502. Further, a "CONFIRM" button 1504, as a user interface, is provided in the "UNREGISTERED" message window 1502.

Figure 16:
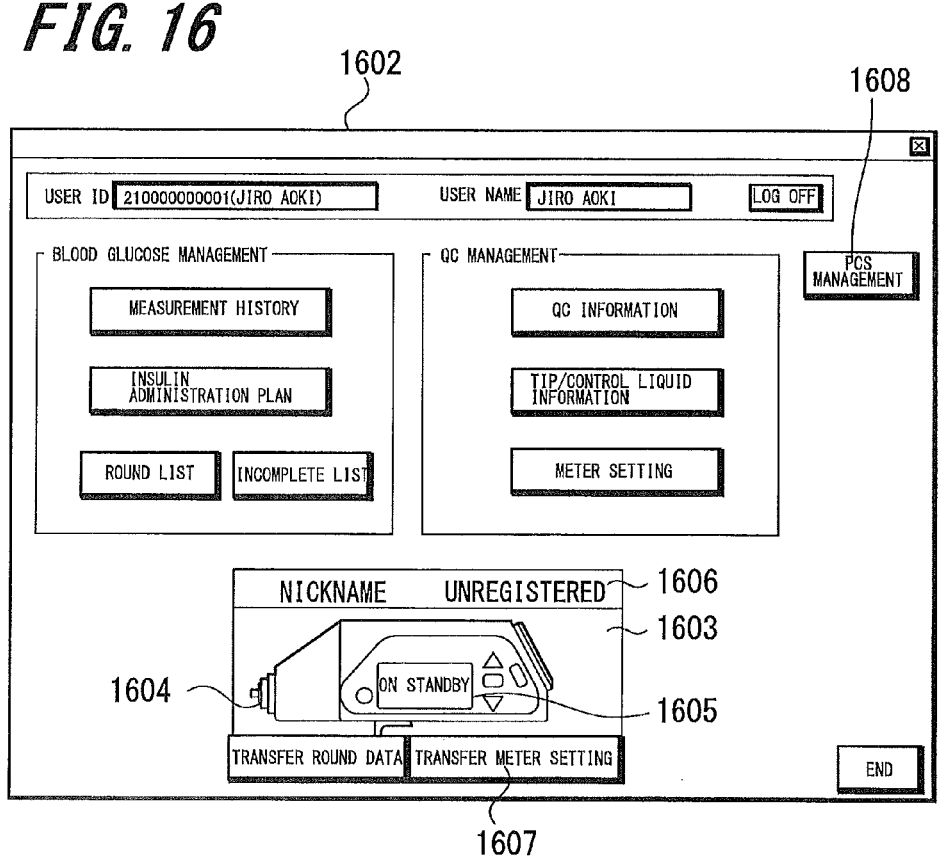
FIG. 16 is a view showing a main menu window.

FIG. 16 is a view showing the main menu window displayed on the display 907 in Step S1408 and Step S1412 of FIG. 14.

A blood glucose meter state display column 1603 is provided in the central lower portion of a main menu window 1602. An illustration 1604 of the blood glucose meter 102 is displayed on the blood glucose meter state display column 1603. A portion of the illustration 1604 corresponding to the LCD is a connection state display column 1605.

In FIG. 16, since the nickname of the blood glucose meter 102 is not registered in the record corresponding to the serial number of the blood glucose meter 102 mounted on the cradle 103 of the blood glucose meter individual setting table 1106 ("NO" in Step S1405, or "NO" in Step S1410 of FIG. 14), a character string "UNREGISTERED" is displayed in a nickname display column 1606.

Figure 17:
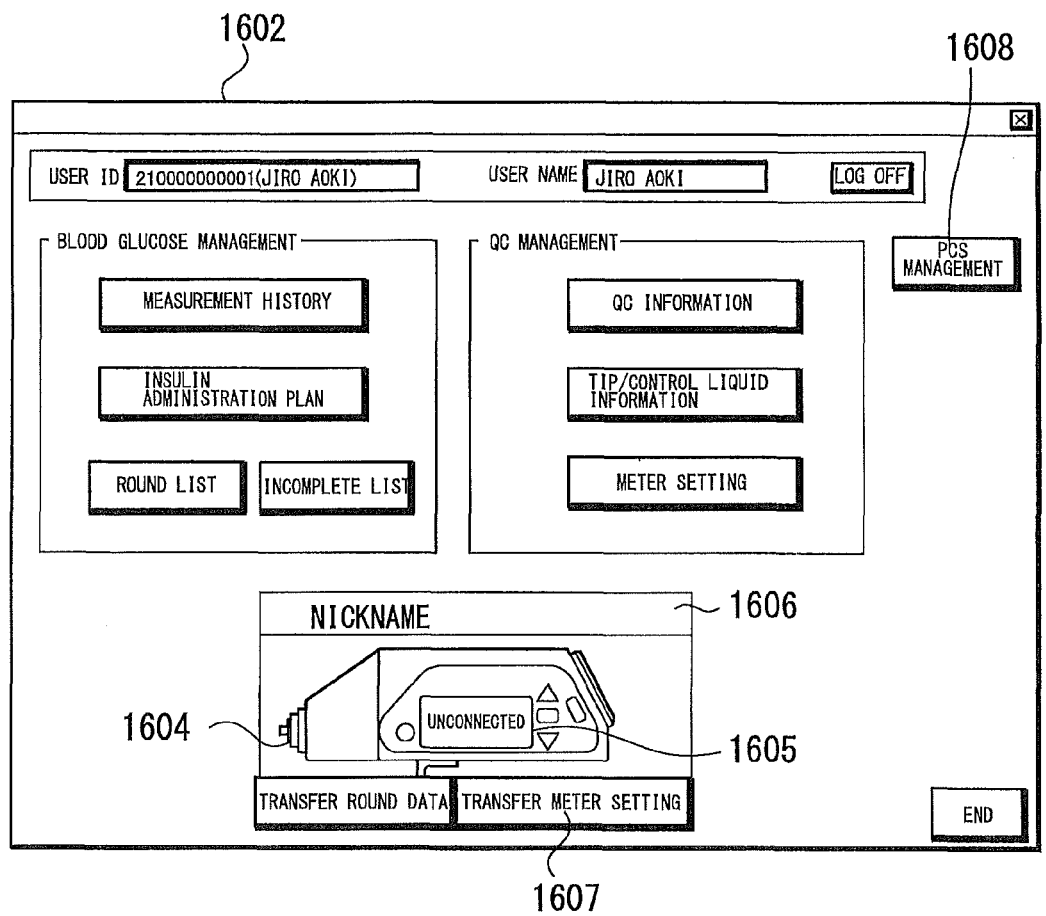
FIG. 17 is a view showing another main menu window.

FIG. 17 is a view showing the main menu window displayed on the display 907 in Step S1304 of FIG. 13.

In FIG. 17, since the blood glucose meter 102 is not mounted on the cradle 103, a character string "UNCONNECTED" is displayed in the connection state display column 1605, and nothing is displayed in the nickname display column 1606.

Figure 18:
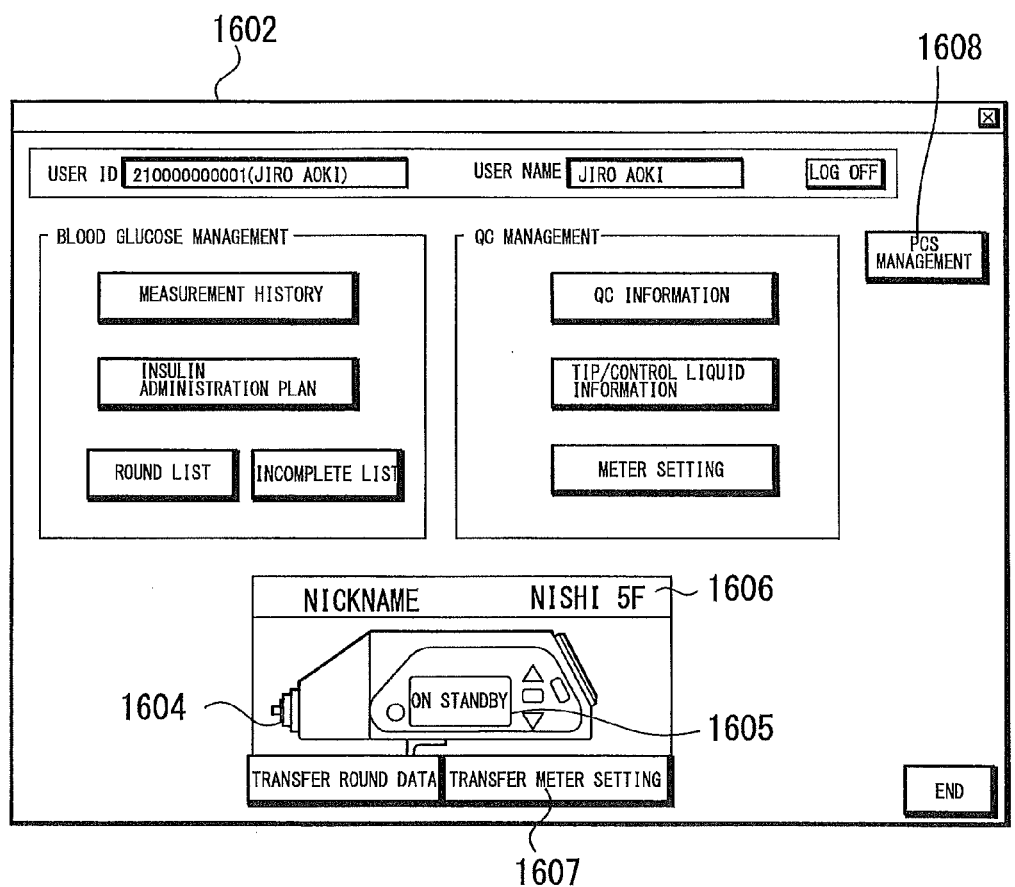
FIG. 18 is a view showing another main menu window.

FIG. 18 is a view showing the main menu window displayed on the display 907 in Step S1411 of FIG. 14.

In FIG. 18, since the nickname of the blood glucose meter 102 is registered in the record corresponding to the serial number of the blood glucose meter 102 mounted on the cradle 103 of the blood glucose meter individual setting table 1106 ("YES" in Step S1410 of FIG. 14), a character string "NISHI 5F", as a nickname, is displayed in the nickname display column 1606.

FIG. 19 is a view showing the meter setting transfer window.

When a "TRANSFER METER SETTING" button 1607 shown in FIG. 16 and FIG. 18 is pressed, a meter setting transfer window 1902 will be displayed on the display 907.

A "METER SERIAL NUMBER" column 1903 is adapted to display the serial number of the blood glucose meter 102. The content of the "METER SERIAL NUMBER" column 1903 can not be changed.

A "NICKNAME" column 1904 is a column adapted to display the nickname of the blood glucose meter 102 and is also an input column whose content can be changed.

A "FUNCTION SETTING" column 1905 is formed by a plurality of items each with checkboxes. These items are each a flag of one bit.

By pressing a "TRANSFER" button 1906, the contents described in the aforesaid columns are transmitted to the blood glucose meter 102 as basic data, as well as stored in the blood glucose meter individual setting table 1106 as operating environment setting value of the blood glucose meter 102.

FIG. 20 is a view showing a nickname management window.

The nickname management window is displayed by pressing a "PCS MANAGEMENT" button 1608 shown in FIGS. 16, 17 and 18 and performing a predetermined operation.

The nickname management window is a screen for deleting the record of the blood glucose meter 102 registered in the blood glucose meter individual setting table 1106 of the measurement data managing device 104. A blood glucose meter display column 2003 is displayed in a nickname management window 2002. The blood glucose meter display column 2003 includes a "SERIAL NUMBER" field and a "NICKNAME" field. The contents of these fields are identical to the contents of the "SERIAL NUMBER" field and the "NICKNAME" field of the blood glucose meter individual setting table 1106.

In the following description, a certain hospital will be used as an example.

The said certain hospital has one nurses' station in which a measurement data managing device 104 is provided. The nurse uses one blood glucose meter 102 to perform round operation for each ward under his/her charge.

It is supposed that the number of the wards has been increased in response to increased number of diabetic patients.

In such a case, if there is only one nurses' station, the nurses' operation will be affected, therefore a branch of the nurses' station is created.

If a new measurement data managing device 104 has been provided in the branch, there is a possibility that some of the blood glucose meters 102 registered in the previous measurement data managing device 104 need to be registered in the new measurement data managing device 104. At this time, it is necessary to delete the record of the blood glucose meter 102 in the nickname management window.

It is difficult to distinguish a plurality of blood glucose meters 102 having almost the same appearance from each other by the serial number only. However, by assigning a nickname to each blood glucose meter 102, it can be easy to identify the plurality of blood glucose meters 102. Being easy to identify the plurality of blood glucose meters 102 means the plurality of blood glucose meters 102 can be correctly used without being confused with each other.

[Nickname Display Function of Blood Glucose Meter 102]

Nickname display function of the blood glucose meter 102 will be described below with reference to FIG. 21.

Figure 21:
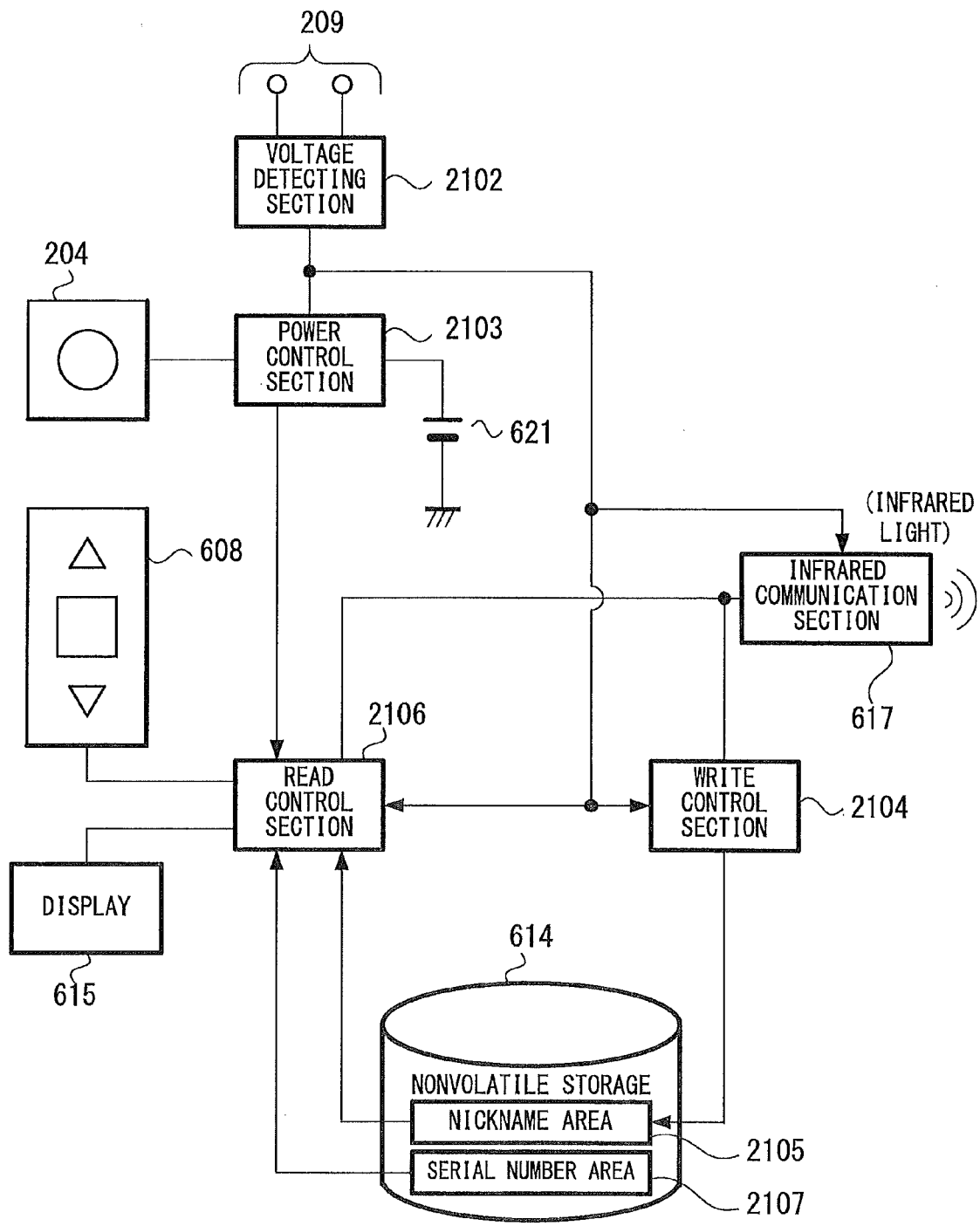
FIG. 21 is a functional block diagram of the blood glucose meter.

FIG. 21 is a functional block diagram of the blood glucose meter 102. Note that, in the present embodiment, only the function of the blood glucose meter 102 associated with the nickname will be described, although the blood glucose meter 102 also has various other functions not included in the disclosure of the present embodiment.

Upon detecting the connection between the power terminal 209 and the charging terminal 402 of the cradle 103, a voltage detecting section 2102 outputs a detection signal.

Upon receiving the detection signal, a power control section 2103 starts to charge the battery 621.

Upon receiving the detection signal, the infrared communication section 617 starts to communicate with the cradle 103.

Upon receiving the detection signal, a write control section 2104 receives a command from the measurement data managing device 104 through the infrared communication section 617 and the cradle 103. If the command is a nickname write instruction issued to the write control section 2104, the received nickname will be recorded in a nickname area 2105 of the nonvolatile storage 614.

Upon receiving the detection signal, a read control section 2106 receives a command from the measurement data managing device 104 through the infrared communication section 617 and the cradle 103. If the command is a nickname read-out instruction issued to the read control section 2106, the nickname will be read out from the nickname area 2105 of the nonvolatile storage 614, and at the same time, the serial number will be read out from a serial number area 2107, and the read nickname and serial number will be transmitted to the measurement data managing device 104.

Herein, the nickname is written in the nickname area 2105 only when the write control section 2104 has received a predetermined instruction from the measurement data managing device 104. Thus, the content of the nickname area 2105 can not be changed by the operating section 608.

Further, the serial number area 2107 is only recorded when the blood glucose meter 102 is shipped from the factory, and the content of the serial number area 2107 can not be changed either by the measurement data managing device 104 or by the operating section 608.

Further, upon being notified by the power control section 2103 that the power switch 204 is pressed and the power is turned on, the read control section 2106 reads out the nickname from the nickname area 2105 of the nonvolatile storage 614, and displays the nickname on the display 907.

Further, upon detecting that about 0.5 seconds has elapsed since the both Cursor keys 205 of the operating section 608 are pressed at the same time, the read control section 2106 reads out the nickname from the nickname area 2105 of the nonvolatile storage 614, and displays the nickname on the display 907.

Figure 22:
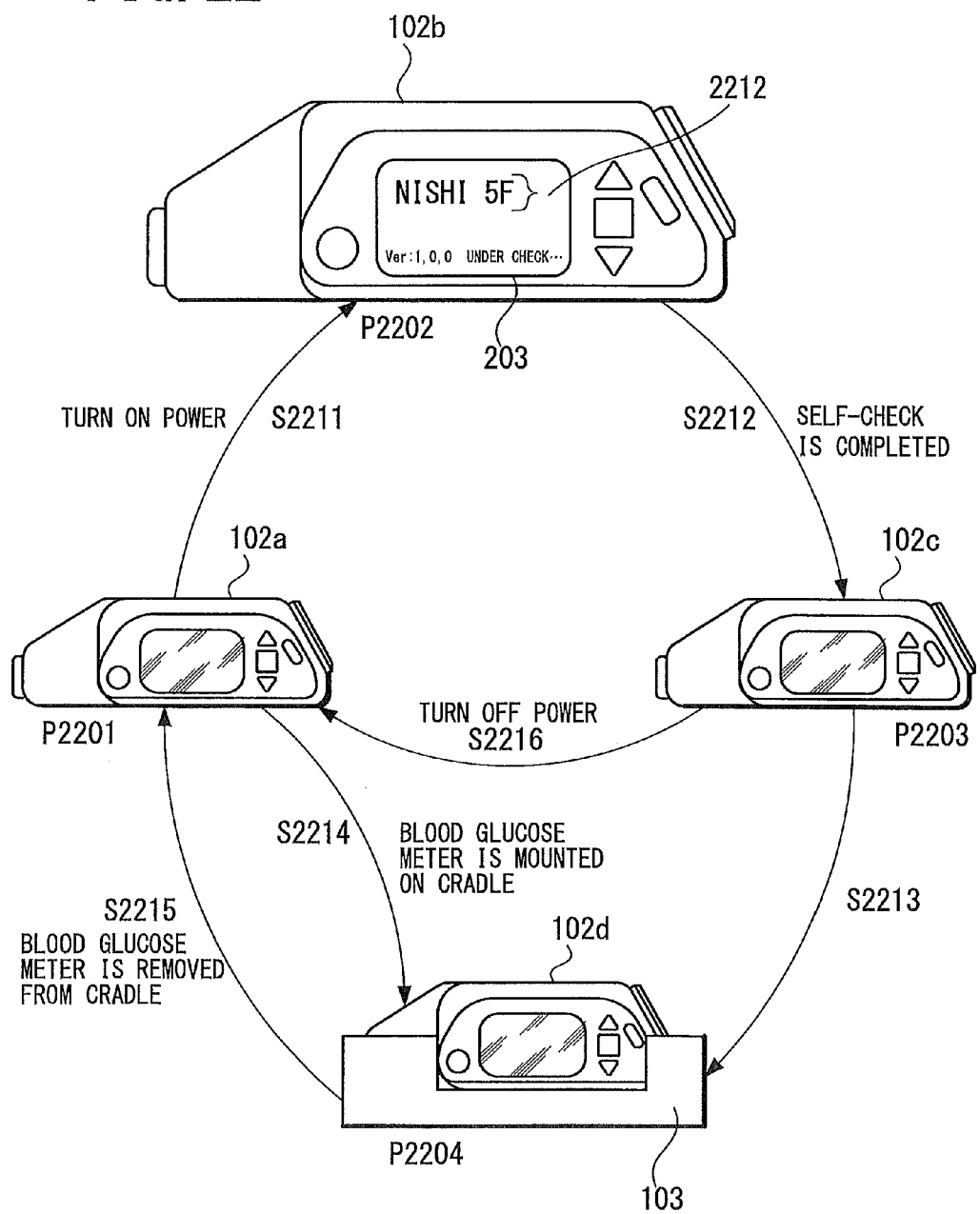
FIG. 22 is a state transition diagram of the blood glucose meter.

FIG. 22 is a state transition diagram of the blood glucose meter 102.

A blood glucose meter 102a is removed from the cradle 103, and is in a power-off state (P2201). In such a state, when pressing the power switch 204 (Step S2211), the nickname of the blood glucose meter 102a will be displayed on the LCD 203 (P2202). At this time, a self-check operation is performed inside a blood glucose meter 102b. When the self-check is completed (Step S2212), a nickname display 2212 on the LCD 203 is erased, and a predetermined menu screen is displayed (P2203).

No matter a blood glucose meter 102c is in a power-on state (P2203) or a power-off state (P2201), once it is mounted on the cradle 103 (P2203→S2213→P2204, P2201→S2214→P2204) and then picked up from the cradle 103 (S2215), it will be brought into a power-off state (P2201).

Figure 23:
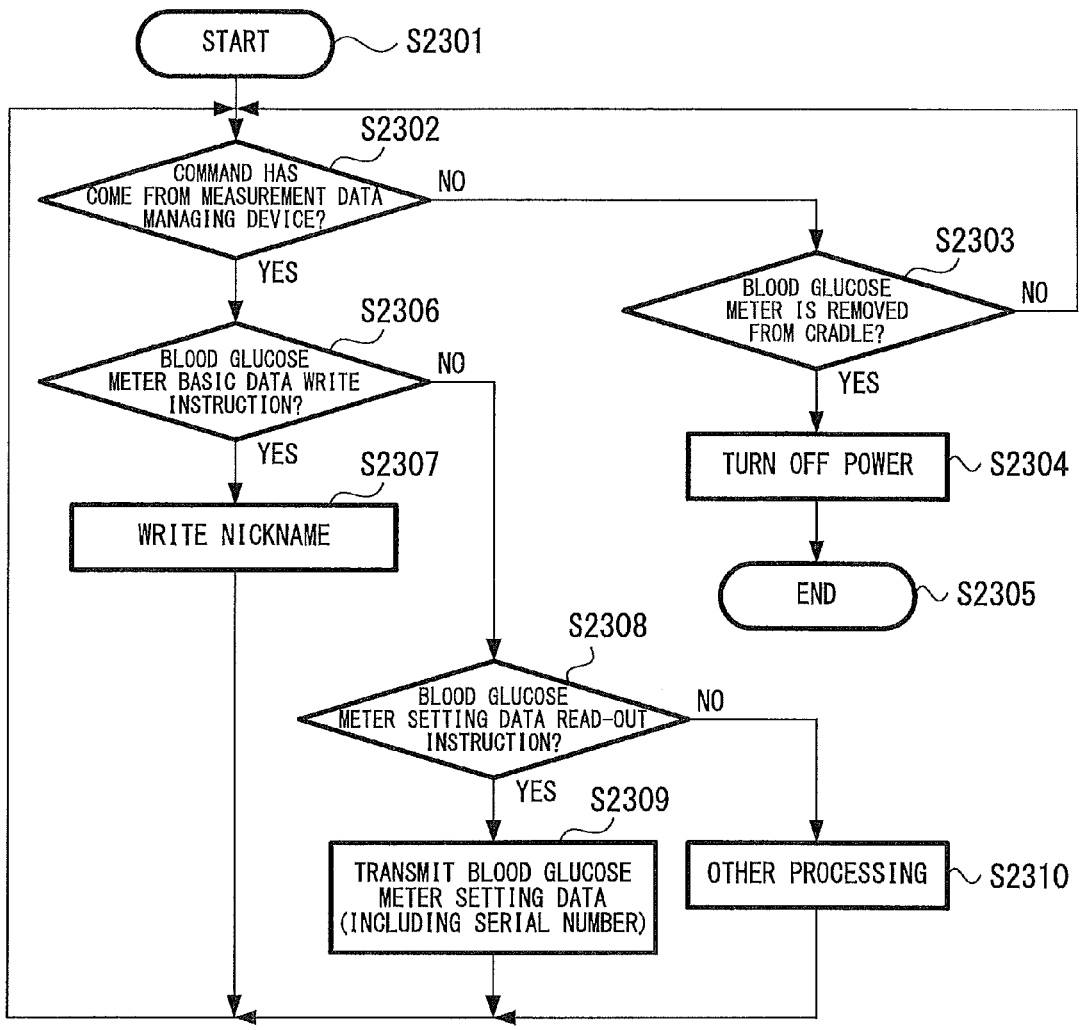
FIG. 23 is a flowchart showing the operation flow when the blood glucose meter is being mounted on the cradle.

FIG. 23 is a flowchart showing the operation flow when the blood glucose meter 102 is being mounted on the cradle 103.

When the blood glucose meter 102 is mounted on the cradle 103, a program for performing the processing shown in FIG. 23 is run (Step S2301).

First, the read control section 2106 and the write control section 2104 confirm whether or not the command has come from the measurement data managing device 104 (Step S2302). If the command has not come, the voltage detecting section 2102 confirms whether or not the blood glucose meter 102 is removed from the cradle 103 (Step S2303). If the blood glucose meter 102 is removed from the cradle 103, the power control section 2103 controls to turn off the power (Step S2304), and the processing is terminated (Step S2305).

If the command has come from the measurement data managing device 104, the read control section 2106 and the write control section 2104 confirm whether or not the command are issued for them.

Next, the write control section 2104 confirms whether or not the command is a blood glucose meter basic data 117 write instruction (Step S2306). If the command is the write instruction, the write control section 2104 will writes the nickname in the nickname area 2105 (Step S2307).

Next, if the command is not the blood glucose meter 102 basic data write instruction ("NO" in Step S2306), the read control section 2106 will confirm whether or not the command is a blood glucose meter setting data 113 read-out instruction (Step S2308). If the command is the read-out instruction, the read control section 2106 will read out the nickname from the nickname area 2105, as well as read out the serial number from the serial number area 2107, and transmits the read nickname and serial number to the measurement data managing device 104 through the infrared communication section 617 and the cradle 103 (Step S2309).

If the command is not the blood glucose meter setting data 113 read-out instruction ("NO" in Step S2308), the read control section 2106 and the write control section 2104 will perform processing corresponding to the case where it is recognized that the command is issued for them (Step S2310).

As described above, the blood glucose meter 102 performs processing corresponding to the command coming from the measurement data managing device 104 until it is removed from the cradle 103. When no command comes from the measurement data managing device 104, the blood glucose meter 102 waits for the command. During such processing, the reading operation or writing operation is performed on the nickname area 2105 in response to the command associated with the nickname.

Figure 24:
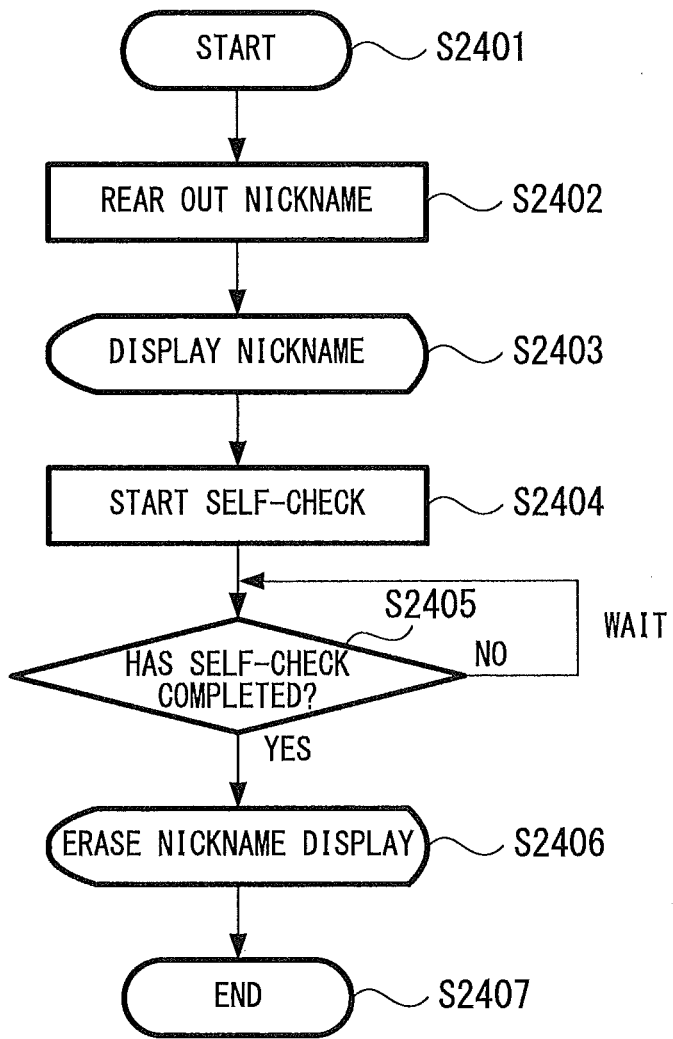

FIG. 24 is a flowchart showing processing of the blood glucose meter 102 when the power is turned on.

When the power is turned on, the program is read from the ROM to the RAM of the microcomputer, and processing of the program is started (Step S2401), the read control section 2106 knows from the power control section 2103 that the power in turned on. The read control section 2106 reads out the nickname from the nickname area 2105 (Step S2402), and displays the nickname on the display 907 (Step S2403).

Next, the self-check operation is started. The self-check operation means an operation for verifying whether or not each functional section inside the blood glucose meter 102 operates normally. The following checks are performed in the self-check operation.

Battery check (to confirm the remaining battery power)
Temperature check (to confirm if the temperature is in an operation-guaranteed temperature range)
Memory data check (to confirm if there is any abnormality in data stored in the nonvolatile storage 614)
Bar-code check (to confirm if the bar-code reader 208 operates normally)

During the self-check operation, a confirmation for confirming whether or not the self-check has been completed is continuously performed (Step S2405). When the self-check operation has been completed, the nickname displayed on the display 907 will be erased (Step S2406), and the processing will be terminated (Step S2407).

Figure 25:
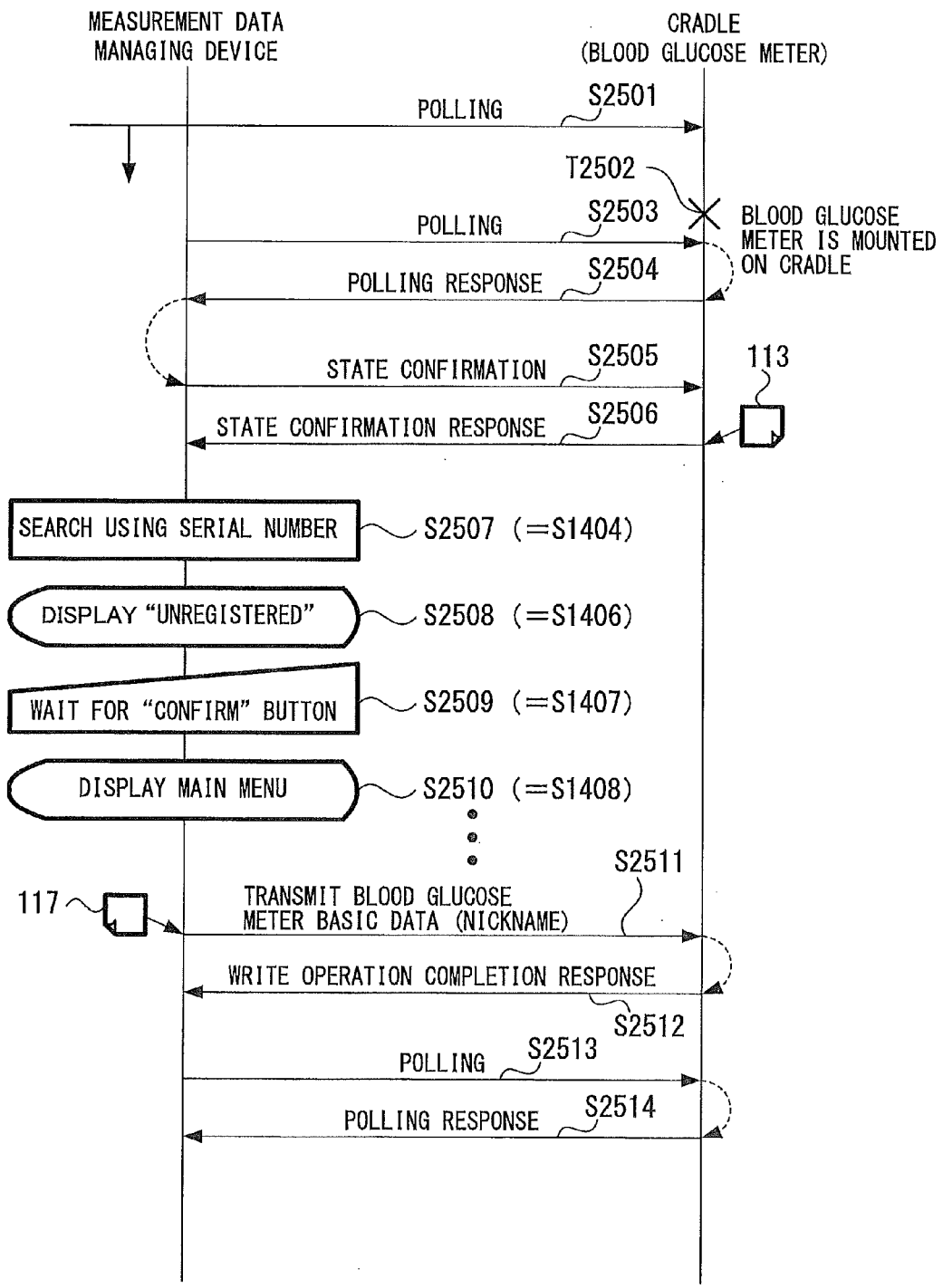
FIG. 25 is a view schematically showing the flow of the communication between the measurement data managing device and the blood glucose meter through the cradle.

FIG. 25 is a view schematically showing the flow of the communication between the measurement data managing device 104 and the blood glucose meter 102 through the cradle 103. Particularly, FIG. 25 is made to describe the operation at the time when an unregistered blood glucose meter 102 is being connected to the measurement data managing device 104.

The measurement data managing device 104 transmits a polling command to the cradle 103 at an interval of 100 msec (Step S2501).

In a state where the blood glucose meter 102 is not mounted on the cradle 103, since no response is sent from the blood glucose meter 102, the measurement data managing device 104 recognizes that the blood glucose meter 102 is not mounted on the cradle 103.

When the blood glucose meter 102 is mounted on the cradle 103 at time T2502, the blood glucose meter 102 will send a polling response command (Step S2504) in response to a polling command sent by the measurement data managing device 104 shortly after the blood glucose meter 102 has been mounted (Step S2503). It can be said that the communication between the measurement data managing device 104 and the blood glucose meter 102 is established at the time when the polling response command is sent in Step S2504.

By receiving the polling response command sent from the blood glucose meter 102, the measurement data managing device 104 recognizes that the blood glucose meter 102 is mounted on the cradle 103. In response to the polling response command, the measurement data managing device 104 transmits a state confirmation command to the blood glucose meter 102 (Step S2505). In response to the state confirmation command, the blood glucose meter 102 transmits the blood glucose meter setting data 113 to the measurement data managing device 104 (Step S2506).

The measurement data managing device 104 takes out the serial number from the received blood glucose meter setting data 113. Further, the measurement data managing device 104 searches the blood glucose meter individual setting table 1106 using the serial number (Step S2507, corresponding to Step S1404 of FIG. 14). As a result of the search, if there is no the serial number in the blood glucose meter individual setting table 1106 ("NO" in Step S1405 of FIG. 14), an "UNREGISTERED" message window will be displayed (Step S2508, corresponding to Step S1406 of FIG. 14). Further, pressing operation of the "CONFIRM" button is waited (Step S2509, corresponding to Step S1407 of FIG. 14). When the "CONFIRM" button is pressed, a main menu is displayed which says that the nickname is unregistered (Step S2510, corresponding to Step S1408 of FIG. 14).

Next, when the user presses the "TRANSFER METER SETTING" button 1607 shown in FIGS. 16 and 18, the meter setting transfer window 1902 shown in FIG. 19 will be displayed on the display 907.

Further, when the user fills the nickname in the "NICKNAME" column 1904 and presses the "TRANSFER" button 1906, the nickname written in "NICKNAME" column 1904 and the set items written in the "FUNCTION SETTING" column 1905 are transmitted from the measurement data managing device 104 to the blood glucose meter 102 as the blood glucose meter basic data 117 (Step S2511). Incidentally, the set contents identical to those of the blood glucose meter basic data 117 are also recorded in the blood glucose meter individual setting table 1106.

The blood glucose meter 102 records the received blood glucose meter basic data 117 in a predetermined area of the nonvolatile storage 614. Among the blood glucose meter basic data 117, the nickname is recorded in the nickname area 2105. When record is completed, the blood glucose meter 102 returns a message to the measurement data managing device 104 to tell it that the write operation is completed (Step S2512).

As described above, the nickname of the blood glucose meter 102 can only be recorded from the measurement data managing device 104 according to user's intention.

The present embodiment includes application examples such as the following.

(1) A program can be configured in such a manner that the nickname display immediately after power-on does not disappear even when the self-check is completed, and the nickname display is erased by pressing an arbitrary key. In such a case, since the nickname is continuously displayed unless an arbitrary key is pressed, it is possible to display the nickname until immediately before use, so that the blood glucose meter can be clearly distinguished from the other blood glucose meters.

The timing for displaying the nickname of the blood glucose meter is not limited to the time when the power is turned on and the time when a specific key operation is performed. It is possible to make the nickname constantly displayed on a small photo arranged at a corner (such as the bottom-left corner) of the LCD 203 (the display 615) even while the blood glucose meter is in operation such as performing blood glucose measurement, insulin dosage display or the like.

The blood glucose meter and the blood glucose level managing system using the blood glucose meter are disclosed in the present embodiment.

It is supposed that a plurality of blood glucose meters for ward use are used in one hospital. In such case, if a plurality of blood glucose meters of the same shape are placed adjacent to each other, it will be difficult for the user to know which one he (or her) should use by appearance. However, considering that the blood glucose meter is used in hospital ward, the method of sticking a seal or the like is not preferable from hygiene standpoint.

The blood glucose meter according to the present embodiment has a nickname area provided in the nonvolatile storage thereof, and a nickname can be recorded in the nickname area. Further, the nickname is displayed in the LCD making use of the time while the self-check is performed when turning on the power. Owing to this configuration, the blood glucose meter can be identified when turning on power.

Further, the program of the blood glucose meter is configured in a manner in which the power of the blood glucose meter is surely turned off when the blood glucose meter is removed from the cradle. By configuring the program of the blood glucose meter in such a manner, when picking up the blood glucose meter from the cradle for use, the user has to operate the power switch to turn on the power under compulsion. At this time, the nickname is displayed on the LCD. Thus, it is possible to compel the user to visually confirm the nickname when starting to use the blood glucose meter, and therefore prevent mistaking of the blood glucose meter.

Further, in order to be able to confirm the nickname even during round, the program of the blood glucose meter is configured in a manner in which the nickname can be displayed by a performing a specific key operation, such as long-pressing the both Cursor keys at the same time. Thus, since it is possible for the user to visually confirm the nickname even while the blood glucose meter is in use, accident of mistaking the blood glucose meter can be prevented. Further, this function provides a feeling of safety to the user such as a nurse whose work burden is very heavy.

If the nickname for the blood glucose meter can written from the blood glucose meter, it will be possible to cause accident of mistaking the blood glucose meter. For this reason, the program is configured in a manner in which the nickname for the blood glucose meter can only be written from the measurement data managing device. In other words, the program is configured in a manner in which the program inside the blood glucose meter for performing nickname writing can only be ran by a command sent from the measurement data managing device. Thus, accident of mistaking the blood glucose meter can be prevented by imposing a restriction on nickname writing.

Although the blood glucose meter can be uniquely identified by the serial number, there is no reason for the user to remember the serial number. To solve this problem, in the measurement data managing device, the serial number and the nickname are associated with each other and registered, along with the set values, in the blood glucose meter individual setting table. Further, when the blood glucose meter is mounted on the cradle and the communication between the blood glucose meter and the measurement data managing device is established, the serial number will be read out from the blood glucose meter, the blood glucose meter individual setting table will be searched with the serial number to read out the nickname, and the nickname will be displayed on the display. Owing to such a configuration, the user can easily identify the blood glucose meter handled by the measurement data managing device.

Further, when deleting the record of the blood glucose meter once having been registered in the measurement data managing device, the blood glucose meter can be easily identified owing to the existence of the nickname.

Although the present embodiment of the present invention is described above, it should be noted that the present invention is not limited to the above embodiment but includes various other modifications and applications without departing from the spirit of the claims of the present invention.

Explanation Of Reference Numerals 102 blood glucose meter
103 cradle
104 measurement data managing device
105 USB cable
112 patient measurement table
113 blood glucose meter setting data
114 patient table
115 user table
116 tip lot table
117 blood glucose meter basic data
202 optical measuring section
203 LCD
204 power switch
205 Cursor keys
206 Enter key
207 bar-code key
208 bar-code reader
209 power terminal
210 infrared communication window
211 battery lid
212 measuring tip
302 eject lever
402 charging terminal
403 infrared communication window
602 CPU
603 ROM
604 RAM
605 bus
606 thermistor
607 calendar clock
608 operating section
609 light-emitting diode
610 driver
611 D/A converter
612 phototransistor
613 A/D converter
614 nonvolatile storage
615 display
616 buzzer
617 infrared communication section
618 power circuit
702 CPU
703 ROM
704 RAM
717 infrared communication section
706 USB interface
718 charging circuit
705 bus
902 bus
903 CPU
904 ROM
905 RAM
906 nonvolatile storage
907 display
908 USB interface
909 operating section
1002 patient
1003 patient ID
1004 nurse
1005 user ID
1006 box
1007 tip lot number
1008 syringe
1009 prescription table
1202 blood glucose meter detecting section
1203 blood glucose meter operating section
1204 user interface control section
1205 table input/output section
1206 blood glucose meter individual setting table
1207 patient information table
1502 "UNREGISTERED" message window
1503 message
1504 "CONFIRM" button
1602 main menu window
1603 blood glucose meter state display column
1604 illustration
1605 connection state display column
1606 nickname display column 1902 meter setting transfer window
1903 "METER SERIAL NUMBER" column
1904 "NICKNAME" column
1905 "FUNCTION SETTING" column
1906 "TRANSFER" button
2002 nickname management window
2003 blood glucose meter display column
2102 voltage detecting section
2103 power control section
2104 write control section
2105 nickname area
2106 read control section
2107 serial number area

The invention claimed is:

1. A blood glucose level managing system comprising:
a blood glucose measuring device; and
a measurement data managing device,
wherein the blood glucose measuring device comprises:
a nonvolatile storage having a serial number area in a predetermined area therein for storing a serial number and a nickname area in a predetermined area therein for storing a nickname;
a read control section adapted to read out the serial number from the serial number area upon receiving a predetermined instruction; and
a first communication section connected to the read control section and adapted to perform data communication with an external device, and
wherein the measurement data managing device comprises:
a second communication section adapted to perform communication with the first communication section;
a blood glucose measuring device individual setting table having a serial number field for storing the serial number and a nickname field for storing the nickname for identifying the blood glucose measuring device;
a blood glucose measuring device detecting section connected to the second communication section and adapted to detect the establishment of the communication between the first communication section and the second communication section;
a blood glucose measuring device operating section adapted to acquire the serial number and the nickname by transmitting, in response to the fact that the blood glucose measuring device detecting section has detected the establishment of the communication between the first communication section and the second communication section, the predetermined instruction to the read control section to instruct it to read out the serial number from the serial number area, and searching the blood glucose measuring device individual setting table using the serial number received from the read control section; and
a first display adapted to display the nickname acquired by the blood glucose measuring device operating section;
wherein the blood glucose measuring device further comprises a write control section adapted to record the nickname in the nickname area when the first communication section and the second communication section are connected with each and the nickname is received from the measurement data managing device through the first communication section.

2. The blood glucose level managing system according to claim 1,
wherein the write control section is connected to the first communication section
wherein the measurement data managing device further includes a measurement data managing device operating section adapted to receive operation conducted by a user;
wherein the blood glucose measuring device operating section transfers the nickname set by the measurement data managing device operating section to the second communication section; and
wherein the second communication section transmits the predetermined instruction and the nickname to the first communication section.

3. The blood glucose level managing system according to claim 2,
wherein the blood glucose measuring device further includes:
a power switch;
a power control section adapted to receive the operation of the power switch and control power on/off; and
a second display adapted to display a predetermined character string and the like, and
wherein the read control section reads out the nickname from the nickname area in response to a power-on state notification issued from the power control section, and controls the second display to display the nickname.

4. The blood glucose level managing system according to claim 3,
wherein the blood glucose measuring device further includes:
a power terminal; and
a voltage detecting section adapted to detect the voltage applied to the power terminal, and
wherein the power control section performs power-off control in response to the fact that the voltage detecting section no longer detects the voltage after detecting the voltage.

5. The blood glucose level managing system according to claim 3,
wherein the blood glucose measuring device operating section is connected to the read control section; and
wherein the read control section reads out the nickname from the nickname area in response to a predetermined operation performed from the blood glucose measuring device operating section, and controls the second display to display the nickname.

6. A blood glucose measuring device comprising:
a power switch;
a power control section adapted to receive the operation of the power switch and control power on/off;
a nonvolatile storage having a serial number area in a predetermined area therein for storing a non-rewritable serial number and a nickname area in a predetermined area therein for storing a writable nickname;
a display adapted to display a predetermined character string;
a read control section adapted read out the serial number from the serial number area upon receiving a predetermined instruction;
a communication section connected to the read control section and adapted to transmit the serial number to an external device; wherein the external device is adapted to receive the serial number and determine a nickname associated with the received serial number; and wherein the external device is adapted to transmit the determined nickname to the measuring device over the communication section; and
a write control section adapted to record the transmitted nickname in the nickname area only when the transmitted nickname is received from the external device connected through the communication section; wherein the read control section is further adapted to read out the recorded nickname from the nickname area in response to a power-on state notification issued from the power control section and control the display to display the recorded nickname.

7. The blood glucose measuring device according to claim 6, further comprising:

a power terminal; and a voltage detecting section adapted to detect the voltage applied to the power terminal, wherein the power control section performs power-off control in response to the fact that the voltage detecting section no longer detects the voltage after detecting the voltage.

8. The blood glucose measuring device according to claim 6, further comprising:

an operating section connected to the read control section, wherein the read control section reads out the nickname from the nickname area in response to a predetermined operation performed from the operating section, and controls the display to display the nickname.

* * * * *